US008039601B1

(12) United States Patent
Aydt et al.

(10) Patent No.: US 8,039,601 B1
(45) Date of Patent: *Oct. 18, 2011

(54) CRYSTALLINE FORMS OF 1,6-BIS [3-(3-CARBOXYMETHYLPHENYL)-4-(2-α-D-MANNOPYRANOSYLOXY)-PHENYL] HEXANE

(75) Inventors: Ewald M. Aydt, Berlin (DE); Remo Kranich, Berlin (DE); Karin Vollhardt, Hennigsdorf (DE); Gerhard Wolff, Glienicke-Nordbahn (DE)

(73) Assignee: Revotar Biopharmaceuticals AG, Hennigsdorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/159,875

(22) Filed: Jun. 14, 2011

Related U.S. Application Data

(63) Continuation of application No. 12/440,300, filed as application No. PCT/EP2007/059410 on Sep. 7, 2007.

(30) Foreign Application Priority Data

Sep. 8, 2006 (EP) ..................................... 06120399

(51) Int. Cl.
A61K 31/7032 (2006.01)
A61K 31/7034 (2006.01)
C07H 15/203 (2006.01)
(52) U.S. Cl. .......................................... 536/18.2; 514/25
(58) Field of Classification Search .......................... None
See application file for complete search history.

(56) References Cited

U.S. PATENT DOCUMENTS

| 5,712,387 | A | 1/1998 | Scott et al. |
| 5,919,768 | A | 7/1999 | Kogan et al. |
| 2002/0132220 | A1 | 9/2002 | Berens et al. |
| 2010/0093653 | A1 | 4/2010 | Aydt et al. |
| 2010/0298245 | A1 | 11/2010 | Aydt et al. |

FOREIGN PATENT DOCUMENTS

| WO | WO9701335 A1 | 1/1997 |
| WO | WO0129054 A3 | 4/2001 |
| WO | WO2008028966 A1 | 3/2008 |
| WO | WO2010115164 A1 | 10/2010 |

OTHER PUBLICATIONS

E. Crockett-Torabi, Selectins and mechanisms of signal transduction, Journal of Leukocyte Biology, 1998, vol. 63, pp. 1-14.
B. Brenner et al., L-Selectin activates the Ras pathway via the tyrosine kinase p56Ick, Proc. Natl. Acad. Sci, USA, 1996, vol. 93, pp. 15376-15381.
Daniel Bock et al., The Role of Selectins During Lung Inflammation and Their Potential Impact for Innovative Therapeutic Strategies, Current Respiratory Medicine Reviews, 2006, vol. 2, pp. 339-354.
Keisuke Okazaki et al., Enhancement of Metastatic Activity of Colon Cancer as Influenced by Expression of Cell Surface Antigens, Journal of Surgical Research, 1998, vol. 78(1), pp. 78-84.
Rodger P. McEver et al., Selectin-carbohydrate interactions during inflammation and metastasis, Glycoconjugate Journal, 1997, vol. 14(5), pp. 585-591.
Rodger P. McEver et al., Perspective Series: Cell Adhesion in Vascular Biology, Role of PSGL-1 Binding to Selctions in Leukocyte Recruitment, J. Clin. Invest., 1997, vol. 100, No. 3, pp. 485-492.
R.P. McEver, 8 Interactions of Selectins with PSGL-1 and Other Ligands, Ernst Schering Res. Found. Workshop, 2004, vol. 44, pp. 137-147.
Gabriela Constantin, The Identification of PSGL-1 as a central proadhesive molecule could help in the design and testing of a more selective therapy to modify the clinical outcome of various inflammatory diseases in humans. PSGL-1 as a Novel Therapeutic Target, Drug News Perspective, 2004, vol. 17(9), pp. 579-586.
Annette M. Muller et al., Heterogeneous expression of cell adhesion molecules by endothelial cells in ARDS, Journal of Pathology, 2002, vol. 198(2), pp. 270-275.
Antonio Di Stefano et al., Upregulation of Adhesion Molecules in the Bronchial Mucosa of Subjects with Chronic Obstructive Bronchitis, Am. J. Respir. Crit. Care. Med., 1994, vol. 149(3), pp. 803-810.
Satomi Terajima et al., An important role of tumor necrosis factor-a in the induction of adhesion molecules in psoriasis, Arch. Dermatol. Res., 1998, vol. 290, pp. 246-252.
Paolo U. Giacomoni et al., A mechanistic model for the aging of human skin, Micron, 2004, vol. 35, pp. 179-184.
P.U. Giacomoni et al., Factors of skin ageing share common mechanisms, Biogerontology, 2004, vol. 2, pp. 219-229.
Scott, Ian L. et al., Stereospecific alpha.-D-mannosylation, Carbohydrate Research, 1999, vol. 317 (1-4), pp. 210-216.
Timothy P. Kogen et al., Novel Synthetic Inhibitors of Selectin-Mediated Cell Adhesion: Synthesis of 1,6-Bis[3-(3-carboxymethylphenyl)-4(2-a-D-mannopyranosloxy) phenyl]hexane (TBC1269), Journal of Medicinal Chemistry, 1998, vol. 41, pp. 1099-1111.
International Search Report (Form PCT/ISA/210) issued in the corresponding application No. PCT/EP2007/059410, completed Oct. 26, 2007 and mailed on Jan. 18, 2008.
Kogen, Timothy P. et al., "Novel Synthetic Inhibitors of Selectin-Mediated Cell Adhesion: Synthesis of 1,6-Bis[3-(3-carboxymethylphenyl)-4(2-a-D-mannopyranosloxy)phenyl]hexane (TBC1269)," Journal of Medicinal Chemistry, 1998, vol. 41, pp. 1099-1111.
Scott, Ian L. et al., "Stereospecific alpha. -D-mannosylation," Carbohydrate Research, 1999, vol. 317 (1-4), pp. 210-216.
Nemoto, Takashi et al., "Small molecule selectin ligand inhibition improves outcome in ischemic acute renal failure," Kidney International, vol. 60, 2001, pp. 2205-2214.
Jayle, C. et al., "Protective role of selectin ligand inhibition in a large animal model of kidney ischemia-reperfusion injury," Kidney International, vol. 69, 2006, pp. 1749-1755.
Ulbrich, Holger et al., "Leukocyte and endothelial cell adhesion molecules as targets for therapeutic interventions in inflammatory disease," Trends in Pharmacological Sciences, vol. 24, No. 12, Dec. 2003, pp. 640-647.

*Primary Examiner* — Eric S Olson
(74) *Attorney, Agent, or Firm* — J.A. Lindeman & Co., PLLC

(57) ABSTRACT

The novel crystalline and polymorphic forms of 1,6-Bis [3-(3-carboxymethylphenyl)-4-(2-α-D-mannopyranosyloxy)-phenyl] hexane have advantageous properties and can be used in pharmaceutical and dermatological compositions.

6 Claims, 17 Drawing Sheets

Figure 6: Amorphous modification of FORM 6

Figure 8: DSC of FORM 2

Figure 9: DSC of FORM 3

Figure 10: DSC of FORM 4

Figure 11: DSC of FORM 5

Figure 12: DSC of FORM 6

Figure 14: TGA of FORM 2

Figure 15: TGA of FORM 3

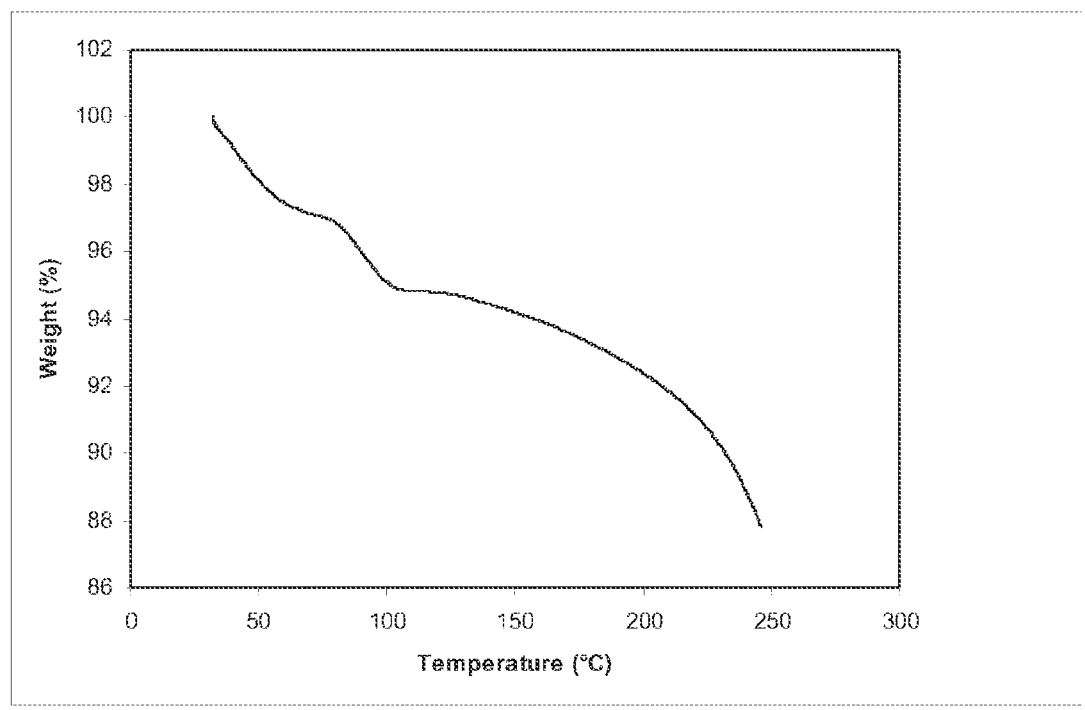
Figure 17: TGA of FORM 6

CRYSTALLINE FORMS OF 1,6-BIS [3-(3-CARBOXYMETHYLPHENYL)-4-(2-α-D-MANNOPYRANOSYLOXY)-PHENYL] HEXANE

The present invention relates to novel crystalline and/or polymorphic forms of 1,6-Bis [3-(3-carboxymethylphenyl)-4-(2-α-D-mannopyranosyloxy)-phenyl] hexane (in particular in its dicarboxylic acid form), processes for their preparation, their use and pharmaceutical compositions comprising them.

Cell-adhesion molecule-mediated functions are part of a complex cascade leading to the migration of circulating white blood cells (leukocytes) from the blood stream into the surrounding tissue (extravasation). Physiologically, leukocyte extravasation is of critical importance for homeostasis and immuno-surveillance of living beings including humans. Lymphocytes for example, are constitutively leaving the blood stream into lymphatic tissues in order to patrol for harmful antigens. Under pathological circumstances however, e.g. local or systemic inflammation and/or injury of the vascular system, this fundamental process is dys-regulated, at least in part, due to an increased surface expression of the adhesion molecules E- and P-selectin. Consequently, the excessive leukocyte extravasation leads to a pathological cellular infiltrate with subsequent tissue damage in several clinically relevant settings.

Disease states such as acute lung injury (ALI), acute respiratory distress syndrome (ARDS), asthma bronchiale (asthma), chronic obstructive pulmonary disease (COPD), psoriasis, rheumatoid arthritis, and sepsis are all associated with tissue inflammation induced and perpetuated by pathologically activated leukocytes infiltrating the respective tissue. In addition, exaggerated leukocyte infiltration contributes to the pathogenesis of ischemic-reperfusion injury (IRI) associated with organ transplantation, cardiopulmonary bypass or percutaneous transluminal angioplasty.

To extravasate, leukocytes must bind to the vascular endothelium in order to finally transmigrate into the surrounding tissue. Therefore, leukocytes have to attach and roll on the endothelium (tethering and rolling). This primary event in extravasation is mediated by the selectin family of cell-adhesion molecules. In addition to directly binding to the endothelium, leukocytes can adhere to other leukocytes, leukocyte-particles, platelets or platelet-derived particles that are already attached to the endothelium.

In addition to rolling and attachment mediated by the interaction of leukocytes and selectins, binding to selectins may also results in signal transduction [E. Crockett-Torabi, J. Leukocyte Biol., 1998, 63, 1-14]. It was shown that small molecules that bind to selectins can induce signal transduction as well [B. Brenner et al., PNAS 1996, 93, 15376-15381].

Furthermore, selectins are also involved in leukocyte retention in lung [D. Bock et al., Curr. Respir. Med. Rev., 2006, 2, 339-354].

The selectin family of adhesion molecules is comprised of three structurally related calcium-dependent carbohydrate binding cell surface proteins, E-, P- and L-selectin. E-selectin is expressed on inflamed endothelium, P-selectin is expressed on inflamed endothelium as well as on platelets and L-selectin is expressed on leukocytes. Selectins are composed of an amino terminal lectin domain, an epidermal growth factor (EGF)-like domain, a variable number of complement receptor-related repeats, a hydrophobic transmembrane domain and a C-terminal cytoplasmic domain. The binding interactions leading to the adhesion of the leukocytes are supposed to be mediated by contact of the lectin domain of the selectins and various carbohydrate ligands on the surface of the leukocytes. All three selectins can bind with low affinity to the carbohydrate sialyl Lewis X (sLe$^X$), a glycosyl moiety present on the surface of most leukocytes. A structurally related glycosyl moiety, sialyl Lewis a (sLe$^a$), is predominantly found on the surface of cancer cells [K. Okazaki et al., J. Surg. Res., 1998, 78(1), 78-84; R. P. McEver et al., Glycoconjugate Journal, 1997, 14(5), 585-591]. In case of P-selectin, a distinct high affinity glycoprotein ligand has been described [R. P. McEver, R. D. Cummings, J. Clin. Invest., 1997, 100, 485-492], the so-called P-selectin glycoprotein ligand-1 (PSGL-1) which contributes to a high affinity selectin binding by its sLe$^X$ moiety as well as by parts of its peptide components, in particular sulphated tyrosine residues [R. P. McEver, Ernst Schering Res. Found. Workshop, 2004, 44, 137-147]. PSGL-1 is one of the most important selectin ligands binding with highest affinity to P-selectin, but it also binds to E- and L-selectin [G. Constantin; Drug News Perspect; 2004; 17(9); 579-586]. It is a homodimeric sialomucin predominantly expressed on leukocytes.

In inflammatory diseases, dys-regulated extravasation is, at least in part, mediated due to an increased cell surface expression of E- and P-selectin. In contrast to their low basal expression, E- and P-selectin expression is upregulated during inflammation, leading to a substantial recruitment of leukocytes into the inflamed tissue. Although selectin-mediated cell adhesion is required for fighting infection, there are various situations in which such cell adhesion is undesirable or excessive, resulting in severe tissue damage instead of repair. In the case of many acute as well as chronic inflammatory disorders (e.g., asthma, COPD, psoriasis, etc.), an association between infiltration of activated leukocytes into the tissue simultaneously with a marked elevation of tissue expression of corresponding adhesion molecules, particularly E- and P-selectin, has been demonstrated [Muller et al., J. Pathol., 2002, 198(2), 270-275; Di Stefano et al., Am. Respir. Crit. Care. Med., 1994, 149(3) 803-810; Terajima et al., Arch. Dermatol. Res., 1998, 290, 246-252].

Leukocyte infiltration may also play a role in inflammatory symptoms in the course of transplant and graft rejection. Also the process of blood clotting is further promoted by leukocyte-leukocyte and leukocyte-platelet binding, which occurs because leukocytes possess both L-selectin and its corresponding ligand P-glycoprotein ligand-1 (PSGL-1) and can thus interact with themselves via PSGL-1, and they can also bind to platelets which carry P-selectin.

In addition, selectins are involved in micro-inflammatory processes causing ageing of the skin [P. U. Giacomoni et al., Micron 2004, 35, 179-184]. The signs of ageing of the skin resulting from the effects on the skin of intrinsic and extrinsic factors are defined by the appearance of wrinkles and fine lines, by the yellowing of the skin which develops a wizened appearance along with the appearance of pigmentation blemishes, by a change in the thickness of the skin, generally resulting in a thickening of the stratum corneum and of the epidermis and a thinning of the dermis, by disorganization of the elastin and collagen fibers which causes a loss of elasticity, of suppleness and of firmness, and by the appearance of telnagiectasia.

Some of these signs are more particularly associated with intrinsic or physiological ageing, that is so to say with "normal" ageing associated with age, whereas others are more specific to extrinsic ageing, that is so to say ageing caused by the environment in general; such ageing is more particularly photo-ageing due to exposure to the sun, to light or to any other radiation. Other factors causing ageing of the skin are atmospheric pollution, wounds, infections, traumatisms, anoxia, cigarette smoke, hormonal status, neuropeptides, electromagnetic fields, gravity, lifestyle (e.g. excessive consumption of alcohol), repetitive facial expressions, sleeping positions, and psychological stressors. Intrinsic and extrinsic factors of ageing of the skin share common mechanisms [P. U. Giacomoni et al., Biogerontology 2004, 2, 219-229]. These factors trigger the micro-inflammatory cycle where selectins are involved.

There is a strong medical, cosmetic (including skin care), and dermatological need for novel highly potent anti-inflammatory and anti-micro-inflammatory compounds for the treatment, prophylaxis, and/or diagnosis of various indications or conditions where inflammatory or micro-inflammatory conditions play a role.

Most of the available anti-inflammatory pharmaceutical therapies, which are available on the market, comprise corticosteroids or NSAIDs (non steroidal anti-inflammatory drugs) having several serious drawbacks/side effects, and target different steps of the inflammatory cascade. Various cosmetic and dermatological compositions (including for skin care) intended inter alia to prevent or treat ageing of the skin are known. However, these compounds also have side effects, consisting of stinging and redness, which the user finds unpleasant. Thus, there remains a need for anti-ageing agents which are at least as effective as the known compounds, but do not exhibit their drawbacks.

Unlike the established strategies to treat, prevent, or diagnose inflammatory or micro-inflammatory indications or conditions, modulating the selectin function is a novel concept intervening the micro-/inflammation cascade at a very early stage and treating, preventing, and/or diagnosing inflammatory or micro-inflammatory indications or conditions according to the present inventions represents a strategy without the drawbacks known from other strategies.

The compound 1,6-Bis [3-(3-carboxymethylphenyl)-4-(2-α-D-mannopyranosyloxy)-phenyl] hexane (compound of the formula (I)) is described, for example, in U.S. Pat. No. 5,919, 768; I. Scott et al., Carbohydrate Research 317 (1-4), 1999, 210-216; T, Kogan et al., J. Medicinal Chemistry 41(7), 1998, 1099-1111; U.S. Pat. No. 5,712,387 and EP-A 0 840 606, which are incorporated herein by reference. The compound of formula I has several valuable pharmacological properties. It acts as pan-selectin antagonist and inhibits leukocyte extravasation. Since leukocyte extravasation is a key step in the pathogenesis of most inflammatory disorders or conditions the compounds of formula (I) offer the opportunity to be developed in a variety of inflammatory and micro-inflammatory indications and conditions. The compound of formula (I) can be used for the prophylaxis, treatment, and diagnosis of inflammatory disorders and for the treatment and prophylaxis of cosmetic and dermatological conditions where micro-inflammatory conditions are involved.

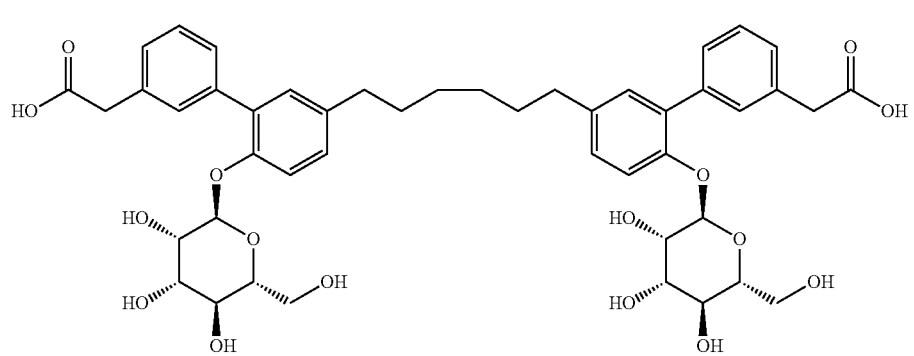

The compound of formula (I) may also be administered to treat other diseases that are associated with cell-cell adhesion. As the compound of formula (I) modulates the binding of E-selectin or P-selectin or L-selectin, any disease that is related to this interaction may potentially be treated by the modulation of this binding interaction.

The compound of formula (I) is also useful for the treatment, diagnosis, and prophylaxis of some forms of cancer, including lung and colon cancer, for instance. Furthermore, the compound of formula (I) can be used for the treatment, diagnosis, and prophylaxis of diseases or conditions where selectins mediated leukocyte retention is involved, e.g. in lung diseases [D. Bock et al., Curr. Respir. Med. Rev., 2006, 2, 339-354].

The compound of formula (I) and its physiologically tolerable salts are suitable as active pharmaceutical ingredients (API) for the prevention, treatment, and diagnosis of various inflammatory or micro-inflammatory diseases or conditions. The compound of formula (I) and/or its physiologically tolerable salts are preferably employed for this in the form of pharmaceutical preparations which are tailored with respect to their composition and the dosage form to the medicinal effects desired in the specific case.

For example it can be used in the form of (1) solid preparations such as tablets (e.g. compressed, layered, sugar, film or enteric coated, chewable, delayed or extended release, sublingual, buccal or effervescent) or capsules (e.g. hard filled or soft gelatine) or in the form of (2) liquid preparations such as oral solutions, emulsions and suspensions, parenteral solutions e.g. for injections and infusions, including lyophilized powders and ready-to-use injections, or ophthalmic solutions or in the form of (3) semi-solid formulations for topical administration such as ointments, creams, gels, or microemulsions.

In addition, specialized formulations like liposomes and related forms, micellar solutions, microspheres, nanoparticles or therapeutic systems, e.g. transdermal therapeutic systems, implants or pumps, inhalative dosage forms, biodegradable or bioerodible polymer systems, surgical or edible foams, soft or hydro gels, microsponges, are also possible dosage forms.

Furthermore the compound of formula (I) may be used for treating ageing of the skin caused by extrinsic and intrinsic factors. The signs of skin ageing are defined by the appearance of wrinkles and fine lines, by the yellowing of the skin which develops a wizened appearance along with the appearance of pigmentation blemishes, by a change in the thickness of the skin, generally resulting in a thickening of the stratum corneum and of the epidermis and a thinning of the dermis, by disorganization of the elastin and collagen fibers which causes a loss of elasticity, of suppleness and of firmness, and by the appearance of telangiectasia.

Surprisingly, it turned out that the compound of formula (I) can occur in a number of different crystal modifications which can be prepared specifically by adjustment of the reaction conditions and/or of the crystallization conditions and which differ in their physicochemical properties. These crystal modifications differ, for example, in their solubility, rate of dissolution or the behavior during pharmaceutical processing and allow the production of pharmaceutical preparations having different property profiles starting from a single parent compound.

The herein described crystalline forms differ from previously described solid forms of the compound of formula (I). According to the published descriptions, the compound of formula (I) has been isolated as white solid with a melting point of 115-117° C. [U.S. Pat. No. 5,919,768, or T. P. Kogan et al., J. Med. Chem. 1998, 41, 1099-1111] indicating, as compared to the melting points indicated below, different solid forms with different physicochemical properties. In the present invention the term "polymorph" is used to describe true polymorphs, amorphous forms, mixtures of polymorphs and pseudo polymorphs, such as hydrates and solvates.

The present invention relates to a polymorph of the compound of formula (I) selected from the group of polymorphs of FORM 1, FORM 2, FORM 3, FORM 4, FORM 5 and FORM 6.

The present invention also relates to a crystalline polymorph which consists of FORM 1 and is further characterized in that it provides an X-ray powder diffraction pattern which shows the following diffraction angles (2Theta) based on cupric $K_{\alpha 1}$ at approximately 4.8° (strong peak). The indicated X-ray diffraction data were obtained from crystal powders at a Stoe powder diffraction system, type P with transmission geometry (STOE & Cie. GmbH, Darmstadt, Germany). Some of the measures are made on a Siemens D5000 diffractometer using Cu $K_{\alpha 1}$ radiation (40 kV, 40 mA). The indicated diffraction angles 2Theta of the X-ray reflections as well as the indicated relative reflection intensities are values rounded to a multiple of 0.5°.

X-ray reflections which have a rounded relative intensity of more than 50% of the intensity of the strongest reflection are designated here as strong X-ray reflections. X-ray reflections which have a rounded relative intensity of 15% or more, but less than or equal 50% of the intensity of the strongest reflection are designated here as medium-strong X-ray reflections. X-ray reflections which have a rounded relative intensity of more than 25% and less or equal 50% of the intensity of the strongest reflection are designated here as stronger medium X-ray reflections.

A crystalline polymorph which consists of FORM 2 is further characterized in that it provides an X-ray powder diffraction pattern for this crystalline form which shows the following diffraction angles (2Theta) based on cupric $K_{\alpha 1}$
  at approximately 5.3° (strong peak),
  at approximately 5.6° (strong peak),
  at approximately 17.4° (strong peak), and
  at approximately 15.1° (medium peak)
is also subject of this invention.

Another embodiment of this invention is a crystalline polymorph which consists of FORM 3 and is further characterized in that it provides an X-ray powder diffraction pattern for this crystalline form which shows the following diffraction angles (2Theta) based on cupric $K_{\alpha 1}$
  at approximately 5.3° (strong peak),
  at approximately 5.6° (strong peak),
  at approximately 4.2° (medium peak),
  at approximately 4.3° (medium peak), and
  at approximately 4.8° (medium peak).

Another embodiment of this invention is a crystalline polymorph which consists of FORM 4 and is further characterized in that it provides an X-ray powder diffraction pattern for this crystalline form which shows the following diffraction angles (2Theta) based on cupric $K_{\alpha 1}$:
  at approximately 16.8° (strong peak),
  at approximately 26.5° (strong peak),
  at approximately 19.7° (stronger medium peak), and
  at approximately 21.5° (stronger medium peak).

Another embodiment of this invention is a crystalline polymorph which consists of FORM 5 and is further characterized in that it provides an X-ray powder diffraction pattern for this crystalline form which shows the following diffraction angles (2Theta) based on cupric $K_{\alpha 1}$:
  at approximately 5.2° (strong peak),
  at approximately 5.6° (strong peak),
  at approximately 21.4° (strong peak),
  at approximately 16.5° (stronger medium peak),
  at approximately 18.7° (stronger medium peak),
  at approximately 20.0° (stronger medium peak), and
  at approximately 20.6° (stronger medium peak).

Another embodiment of this invention is a polymorph which consists of FORM 6 and is further characterized in that it provides an X-ray powder diffraction pattern for this amorphous form which shows the following diffraction angles (2Theta) based on cupric $K_{\alpha 1}$: 19.6° (one broad peak).

A further embodiment of this invention is a crystalline polymorph which consists of FORM 1 and is further characterized in that it provides an X-ray powder diffraction pattern for this crystalline form which shows the following diffraction angles (2Theta) based on cupric $K_{\alpha 1}$
  at approximately 4.8° (strong peak),
  at approximately 16.6° (medium peak), and
  at approximately 16.8° (medium peak).

Another embodiment of this invention is a crystalline polymorph which consists of FORM 2 and is further characterized in that it provides an X-ray powder diffraction pattern for this crystalline form which shows the following diffraction angles (2Theta) based on cupric $K_{\alpha 1}$
  at approximately 5.3° (strong peak),
  at approximately 5.6° (strong peak),
  at approximately 17.4° (strong peak),
  at approximately 9.9° (medium peak),
  at approximately 10.3° (medium peak),
  at approximately 13.8° (medium peak),
  at approximately 15.0° (medium peak),
  at approximately 16.3° (medium peak),
  at approximately 16.6° (medium peak),
  at approximately 18.7° (medium peak),
  at approximately 19.1° (medium peak),
  at approximately 19.2° (medium peak),
  at approximately 19.8° (medium peak),
  at approximately 20.1° (medium peak),
  at approximately 20.4° (medium peak),
  at approximately 20.7° (medium peak),
  at approximately 21.5° (medium peak),
  at approximately 24.3° (medium peak),
  at approximately 24.8° (medium peak),
  at approximately 25.5° (medium peak), and
  at approximately 26.5° (medium peak).

A further embodiment of this invention is a crystalline polymorph which consists of FORM 3 and is further characterized in that it provides an X-ray powder diffraction pattern for this crystalline form which shows the following diffraction angles (2Theta) based on cupric $K_{\alpha1}$ at approximately 5.3° (strong peak),
at approximately 5.6° (strong peak),
at approximately 4.2° (medium peak),
at approximately 4.8° (medium peak),
at approximately 7.2° (medium peak),
at approximately 9.9° (medium peak),
at approximately 10.3° (medium peak),
at approximately 10.6° (medium peak),
at approximately 11.7° (medium peak),
at approximately 13.8° (medium peak),
at approximately 15.1° (medium peak),
at approximately 16.3° (medium peak),
at approximately 16.6° (medium peak),
at approximately 16.9° (medium peak),
at approximately 17.4° (medium peak),
at approximately 18.8° (medium peak),
at approximately 19.1° (medium peak),
at approximately 19.3° (medium peak),
at approximately 19.8° (medium peak),
at approximately 20.0° (medium peak),
at approximately 20.1° (medium peak),
at approximately 20.4° (medium peak),
at approximately 20.7° (medium peak),
at approximately 21.5° (medium peak),
at approximately 24.3° (medium peak),
at approximately 24.8° (medium peak),
at approximately 25.5° (medium peak), and
at approximately 26.5° (medium peak).

Another embodiment of this invention is a crystalline polymorph which consists of FORM 4 and is further characterized in that it provides an X-ray powder diffraction pattern for this crystalline form which shows the following diffraction angles (2Theta) based on cupric $K_{\alpha1}$:
at approximately 4.3° (strong peak),
at approximately 16.8° (strong peak),
at approximately 26.5° (strong peak),
at approximately 11.7° (stronger medium peak),
at approximately 18.2° (stronger medium peak),
at approximately 19.7° (stronger medium peak), and
at approximately 21.5° (stronger medium peak).

Another embodiment of this invention is a crystalline polymorph which consists of FORM 5 and is further characterized in that it provides an X-ray powder diffraction pattern for this crystalline form which shows the following diffraction angles (2Theta) based on cupric $K_{\alpha1}$:

at approximately 5.2° (strong peak),
at approximately 5.6° (strong peak),
at approximately 21.4° (strong peak),
at approximately 10.2° (stronger medium peak),
at approximately 16.5° (stronger medium peak),
at approximately 17.3° (stronger medium peak),
at approximately 18.7° (stronger medium peak),
at approximately 20.0° (stronger medium peak),
at approximately 20.6° (stronger medium peak),
at approximately 23.4° (stronger medium peak), and
at approximately 23.6° (stronger medium peak).

A particular subject of this invention is a crystalline polymorph which provides an X-ray powder diffraction pattern substantially in accordance with FIG. 1.

A crystalline polymorph which provides an X-ray powder diffraction pattern substantially in accordance with FIG. 2 is also subject of this invention.

Another subject of this invention is a crystalline polymorph which provides an X-ray powder diffraction pattern substantially in accordance with FIG. 3.

Another subject of this invention is a crystalline polymorph which provides an X-ray powder diffraction pattern substantially in accordance with FIG. 4.

Another subject of this invention is a crystalline polymorph which provides an X-ray powder diffraction pattern substantially in accordance with FIG. 5.

Another subject of this invention is an amorphous polymorph which provides an X-ray powder diffraction pattern substantially in accordance with FIG. 6.

Two X-ray powder diffraction pattern diagrams are normally substantial in accordance if the strong and medium reflections of both diffraction patterns are identical or show 2Theta angles with a shift of maximal 2Theta±0.2°.

Further details regarding the X-ray diffraction diagrams which can also serve for further characterization of the FORM 1, FORM 2, FORM 3, FORM 4, FORM 5 and FORM 6 are specified below.

The X-ray diffraction diagrams obtained under the conditions indicated are shown in FIGS. 1 to 6. In the figures, the diffraction angle 2Theta (in °) is plotted in the abscissa direction and the relative intensity (in %) is plotted in the ordinate direction.

FORM 1, FORM 2, FORM 3, FORM 4, FORM 5 and FORM 6 of the compound of formula (I) are all white solids which are excellently filterable.

While FORM 1 of the present invention appears as a white powder, what qualifies it for better solubility in several media like water or surfactants (e.g. for the production of a microemulsion) or for powder inhaling, FORM 2 and FORM 3 of the present invention appear as white free flowing solids what qualities them for a comfortable handling during manufacturing processes or for processing them into a medicinal or skin care, cosmetic, or dermatological product. The solids are stable on storage at the customary temperatures and also at medium to higher atmospheric humidity.

Depending on the crystal modification, they have differences in pharmaceutical related properties, e.g. water solubility. Therefore, they are particularly advantageously suitable for use in pharmaceutical preparations, in particular for the production of solid, semi-solid or liquid formulations which are intended, for example, for parenteral administration, but also for the production of pharmaceutical dosage forms to be administered orally or topically.

The invention comprises FORM 1, FORM 2, FORM 3, FORM 4, FORM 5 and FORM 6 of compound of formula (I) both in solvent-free from and in the form of solvates, for example hydrates or adducts with alcohols such as isopropanol or ethanol.

A crystalline polymorph which consists of FORM 1 and provides an infrared spectrum containing peaks at 3404 cm$^{-1}$, 2931 cm$^{-1}$, 1707 cm$^{-1}$, 1500 cm$^{-1}$, 1479 cm$^{-1}$, 1245 cm$^{-1}$, 1228 cm$^{31\ 1}$, 1136 cm$^{-1}$, 1095 cm$^{31\ 1}$, 1050 cm$^{-1}$, 818 cm$^{-1}$, 801 cm$^{-1}$, and 690 cm$^{-1}$ is also subject of this invention.

The present invention also relates to a crystalline polymorph which consists of FORM 2 and provides an infrared spectrum containing peaks at 3246 cm$^{-1}$, 2933 cm$^{-1}$, 1728 cm$^{-1}$, 1478 cm$^{-1}$, 1226 cm$^{-1}$, 1066 cm$^{-1}$, 1017 cm$^{-1}$, 982 cm$^{-1}$, 800 cm$^{-1}$, 686 cm$^{-1}$, and 605 cm$^{-1}$.

The present invention also relates to an amorphous polymorph which consists of FORM 6 and provides an infrared spectrum containing peaks at 3387 cm$^{-1}$, 2928 cm$^{-1}$, 855 cm$^{-1}$, 1710 cm$^{-1}$, 1607 cm$^{-1}$, 1478 cm$^{-1}$, 1223 cm$^{-1}$, 1115 cm$^{-1}$, 977 cm$^{-1}$, 890 cm$^{-1}$, 797 cm$^{-1}$, and 703 cm$^{-1}$.

The pharmacological properties of the polymorphs of compound of formula (I) such as FORM 1, FORM 2, FORM 3, FORM 4, FORM 5 or FORM 6 and their possible uses for the therapy, diagnosis, and/or prophylaxis of disorders are not the same.

However, if the substances are present at the same concentrations in the blood (circulation), in the lymphatic system, in the target organ or in the target cell in dissolved form they tend to have the same properties, independent of the original form of the solid. Thus the polymorphs have corresponding properties to those which are described inter alia in U.S. Pat. No. 5,919,768 and U.S. Pat. No. 5,712,387 and EP-A 0 840 606.

Like the compound of formula (I) as described therein, the polymorphs of compound of formula (I) such as FORM 1, FORM 2, FORM 3, FORM 4, FORM 5 and the amorphous FORM 6 modulate the action of selectins.

The action of FORM 1, FORM 2, FORM 3, FORM 4, FORM 5 and FORM 6 can be investigated, for example, in the pharmacological models which are described in U.S. Pat. No. 5,919,768, U.S. Pat. No. 5,712,387 or EP-A 0 840 606. The activity of the crystalline forms can also be shown by using other methods known in the prior art.

The present invention also relates to the use of a crystalline polymorph of the compound of formula (I) for the preparation of a pharmaceutical composition. Due to the differences in solubility, the polymorphic forms can provide various formulations.

The amount used of a crystalline polymorph of the compound of formula (I) corresponds to the amount required to obtain the desired result using the pharmaceutical compositions.

The amount can be varied to a large extent. It depends on the derivative used, the individual on whom it is applied, and the time of this application. To provide an order of magnitude, in the pharmaceutical compositions according to the invention, the crystalline polymorphs of the compound of formula (I) may be administered in an amount representing from 0.001% to 40% by weight, preferentially 0.005% to 30% by weight and more preferentially from 0.01% to 20% by weight, but depending on the nature of the pharmaceutical preparation the content can also be, for example, higher than 40% by weight.

A pharmaceutical composition comprising a polymorph of compound of formula (I) such as FORM 1, FORM 2, FORM 3, FORM 4, FORM 5 and/or FORM 6 and at least one further pharmaceutically acceptable component is also subject of this invention.

The pharmaceutical composition contains, for example, a polymorph of compound of formula (I), e.g. FORM 1 and a pharmaceutically acceptable component, or FORM 2 and a pharmaceutically acceptable component, or FORM 3 and a pharmaceutically acceptable component, or, for example, two of the crystalline polymorphs according to the invention such as FORM 1 and 2, or FORM 1 and 3, or FORM 2 and 3, in each case together with a pharmaceutically acceptable component.

The pharmaceutical composition can be manufactured using standard technologies, which are known to the person skilled in the art. For this, one or more polymorphs of compound of formula (I) according to the invention are brought into a suitable dosage form together with one or more pharmaceutical components.

The pharmaceutical composition of the present invention may include one or more of the polymorphs of compound of formula (I) formulated together with one or more physiologically acceptable carriers, adjuvants or vehicles, which are collectively referred to herein as components, e.g. for parenteral injection, for oral administration in solid or liquid form, for rectal or topical administration and the like.

The compositions can e.g. be administered to humans and animals either orally, rectally, parenterally (intravenously, intramuscularly, or subcutaneously), intracisternally, intravaginally, intraperitoneally, locally (powders, ointments or drops), or as a buccal or by inhalation (nebulized, or as nasal sprays).

Compositions suitable for parenteral injection may comprise physiologically acceptable sterile aqueous or nonaqueous solutions, dispersions, suspensions or emulsions and sterile powders for reconstitution into sterile injectable solutions or dispersions. Examples of suitable aqueous and non-aqueous carriers, diluents, solvents or vehicles include water, to ethanol, polyol, (propylene glycol, polyethylene glycol, glycerol and the like), suitable mixtures thereof, vegetable oils (such as olive or cannola oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispersing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monostearate and gelatin.

If desired, and for more effective distribution, the crystalline polymorphs of compound of formula (I) can be incorporated into slow or timed release or targeted delivery systems such as polymer matrices, liposomes and microspheres. They may be sterilized, for example, by filtration through a bacteria-retaining filter, or by incorporating sterilizing agents in the form of sterile water, or some other sterile injectable medium immediately before use.

Solid dosage forms for oral administration include capsules, tablets, pills, powders and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol and silicic acid, (b) binders, as for example, carboxymethylcellulose, alginates, gelatin, polyvinylpyrrolidone, sucrose and acacia, (c) humectants, as for example, glycerol, (d) disintegrating agents, as for example, agar-agar, calcium carbonate, potato or tapioca starch, alginic acid, certain complex silicates and sodium carbonate, (e) solution retarders, as for example, paraffin, (f) absorption accelerators, e.g. quaternary ammonium compounds, (g) wetting agents, as for example, cetyl alcohol and glycerol monostearate, (h) adsorbents, as for example, kaolin and bentonite, and (i) lubricants, as for example, talc, calcium stearate, magnesium stearate, solid polyethylene glycols, sodium lauryl sulfate or mixtures thereof. In the case of capsules, tablets and pills, the dosage forms may also comprise buffering agents.

Solid compositions of a similar type may also be employed as fillers in soft and hard-filled gelatin capsules using such excipients as lactose or milk sugar as well as high molecular weight polyethylene glycols and the like. Solid dosage forms such as tablets, dragees, capsules, pills and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions that can be used are polymeric substances and waxes.

The active compounds can also be in microencapsulated form, if appropriate, with one or more of the above-mentioned excipients.

Liquid dosage forms for oral administration include pharmaceutically acceptable emulsions, solutions, suspensions, syrups and elixirs. In addition to the active crystalline polymorphs of compound of formula (I), the liquid dosage forms may contain inert diluents commonly used in the art such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, cannola oil, castor oil and sesame seed oil, glycerol, tetrahydrofurfuryl alcohol, polyethylene glycols and fatty acid esters of sorbitan or mixtures of these substances, and the like.

Besides such inert diluents, the compositions can also include adjuvants, such as wetting agents, emulsifying and suspending agents, sweetening, flavoring and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth or mixtures of these substances and the like.

Compositions for rectal administrations are preferably suppositories, which can be prepared by mixing the compounds of the present invention with suitable nonirritating excipients or carriers such as cocoa butter, polyethylene glycol or a suppository wax, which are solid at ordinary temperatures but liquid at body temperature and therefore melt in the rectal or vaginal cavity and release the active pharmaceutical ingredient.

Dosage forms for topical administration of a compound of this invention include ointments, powders, sprays and inhalants.

The active pharmaceutical ingredient is admixed under sterile conditions with a physiologically acceptable carrier and any needed preservatives, buffers or propellants as may be required. Ophthalmic formulations, eye ointments, suspensions, powders and solutions are also contemplated as being within the scope of this invention.

The polymorphs of compound of formula (I) according to this invention can also be administered in the form of liposomes. As is known in the art, liposomes are generally derived from phospholipids or other lipid substances. Liposomes are formed by mono or multilamellar hydrated liquid crystals that are dispersed in an aqueous medium. Any nontoxic, physiologically acceptable and metabolizable lipid capable of forming liposomes can be used. The present compositions in liposome form can contain, in addition to the selectin binding inhibitors of the present invention, stabilizers, preservatives, excipients and the like. The preferred lipids are the phospholipids and the phosphatidyl cholines (lecithins), both natural and synthetic. Methods to form liposomes are well known in the art.

Actual dosage levels of active pharmaceutical ingredient in the compositions of the present invention may be varied so as to obtain an amount of active pharmaceutical ingredient that is effective to obtain the desired therapeutic response for a particular composition and method of administration.

The selected dosage level, therefore, depends on the desired therapeutic effect, on the route of administration, on the desired duration of treatment and other factors.

The total daily dosage of the compounds of this invention administered to a host in single or divided doses may be in the range of about 0.3 mg to about 50 mg per kilogram of body weight. Dosage unit compositions may contain such submultiples thereof as may be used to make up the daily dosage. It will be understood, however, that the specific dose level for any particular patient, whether human or other animal, will depend upon a variety of factors including the body weight, general health, sex, diet, time and route of administration, rates of absorption and excretion, combination with other drugs and the severity of the particular disease being treated.

The pharmaceutical composition comprising at least one polymorph of compound of formula (I) such as FORM 1, FORM 2, FORM 3, FORM 4, FORM 5 and/or FORM 6 can be used for the treatment, diagnosis, and/or prophylaxis of inflammatory diseases or conditions. Thus, another subject of this invention is the use of pharmaceutical composition comprising a (crystalline) polymorph of compound of formula (I) such as FORM 1, FORM 2, FORM 3, FORM 4, FORM 5 or FORM 6 for the treatment, diagnosis and/or prophylaxis of inflammatory diseases or conditions.

Furthermore, the pharmaceutical compositions may comprise additional active pharmaceutical ingredients. The present invention therefore relates to pharmaceutical composition comprising a (crystalline) polymorph of compound of formula (I) such as FORM 1, FORM 2, FORM 3, FORM 4, FORM 5 or FORM 6 and at least one further active pharmaceutical ingredient.

Favorable, but nevertheless optional active pharmaceutical ingredients, which may be used are all active pharmaceutical ingredients customary or suitable for pharmaceutical applications. Exemplary, possible other active pharmaceutical ingredients are other substances having anti-inflammatory activity such as:

histamine receptor targeted molecules (e.g. 2-methylhistamine, dimaprit, or imetit, ketofifen, promethazine), kinin modulators, modulators of eicosanoid synthesis, nonsteroidal anti-inflammatory drugs (NSAIDs) (e.g. aspirin, acetaminophen, ibuprofen, ketoprofen, naproxen, indomethacin, piroxam, diflunisal, celecoxib, apazone), xanthine oxidase targeted molecules (e.g. allopurinol), $\beta_2$ adrenergic receptor targeted molecules (e.g. albuterol, levalbuterol, metaproterenol, terbutaline, pirbuterol, salmeterol xinafoate, formoterol, arformoterol, carmoterol, indacaterol, salbutamol, GSK-159797, GSK-685698, GSK-597901, GSK-159802, 642444, 678007, LAS-34273, LAS-35201, TD-5742), muscarinic receptor modulators (e.g. tiotropiumbromide, ipratropiumbromide, AD237), leukotriene-receptor modulators (e.g. zafirlukast, montelukast, prantukast), $LTB_4$-modulators (e.g. LY293111, SB201146, BIIL315ZW), modulators of $LTB_4$-synthesis (e.g. BAYx1005), modulators of leukotriene synthesis (e.g. zileuton), recombinant monoclonal anti-IgE antibodies (e.g. omalizumab), IL-1 receptor modulators, glucocorticoids (e.g. cortisol, cortisone, prednisolon, dexamethason, betamethason, fluocinoid, fluocortolon, diflucortolon-21-valerat, ciclesonid, roleponide palmitate, mometasone furoate), modulators of $PDE_4$ (e.g. cilomilast, roflumilast, BAY 19-8004, NVP-ABE171), modulators of IL-2 transcription (e.g. ciclosporine A, tacrolismus, sirolismus), modulators of IL-2 receptor (e.g. basiliximab, daclizumab), modulators of retinoid acid receptor (RAR) (e.g. acitretin, tazaroten, adapalen, Ro444753), modulators of RXR (e.g. bexaroten), modulators of CXCR2 (e.g. SB225002, SB265610), modulators of CCR3 (e.g. Ro1164875, Ro3202947), modulators of chemokine receptor (e.g. SB297006, SB238437, UCB35625), modulators of cytokines (e.g. SCH55700, infiximab, etanercept, BION-1), modulators of cytokine receptor (e.g. altrucincept), cytokines (e.g. IL-10, IL-12), modulators of Adenosine receptor (e.g. EPI2010, CGS21680, GW328267), modulators of the complement system (e.g. C5a/C3a receptor antagonists), modulators of the ICAM-family, modulators of VCAM-1, modulators of PECAM-1, modulators of integrins (e.g. natalizumab, efalizumab), modulators of TNF/TNF-receptor (e.g. infliximab, etanercept, adalimumab), modulators of TNF-alpha converting enzyme (TACE) (e.g. PKF 242-484, PKF 241-466), modulators of matrix-metaloproteinase (MMP) (e.g. PKF 242-484, PKF 241-466, BAY 15-7496, RS 113456,), modulators of serine proteases (e.g. ZD0892), modulators of elastases (e.g. ONO 6818), modulators of glycoproteins (e.g. integrilin), modulators of JAM family, modulators of MIF, modulators of signalling pathways (e.g. cilomilast, rofumilast, sildenafil, gefitinib, erlotinib), modulators of NF-kB pathway, modulators of P38 mitogen-activated protein (MAP) kinase pathway (e.g. SB203580, SB239063), modulators of Jak/STAT pathway, modulators of protein kinases (e.g. rapamycin), modulators of proteasome/signalosome (e.g. velcade), modulators of sphingosin-1 phosphate receptor (e.g. FTY720), modulators of IL-17 pathway, modulators of Toll-like receptor, modulators of proliferator-activated receptor (PPAR) (e.g. rosiglitazone), modulators of platelet activating factor (PAF) pathway, modulators of 5HT3 (e.g. ondansetron, granisetron, dolasetron), modulators of INF-γ, modulators of IL2R alpha-chain (e.g. basiliximab, daclizumab), modulators of CD3 (T-cell) (e.g. OKT3=muronomab CD3), modulators of glycosylation, modulators of iNOS, modulators of tryptase (e.g. APC366, AMG-126737, MOL6131), ATP-sensitive potassium channel openers (e.g. SDZ217-744, KCO912), antisense oligonucleotides (e.g. GATA-3), cromolyn sodium, nedocromil sodium, theophylline, polyphenols (e.g. gallic acid and derivates thereof, epicatechins, epigallocatechines), derivatives of vitamin D (e.g. calcitriol, calcipotriol, tacalcitol), all trans retinoic acid (ATRA), derivatives of vitamin A (e.g. tretinoin, isotretinoin), dithranole, azelaic acid, benzolyperoxide, erythromycin, clindamicyn, minocycline, tetracycline, and derivatives of 5-amino-salicylic acid (e.g. sufasalazin, olsalazin).

Possible other advantageous pharmaceutical compositions are also obtained if antioxidants are used as additives or active pharmaceutical ingredients. According to this invention, the pharmaceutical compositions may comprise one or more antioxidants. Favorable, but nevertheless optional antioxidants which may be used are all antioxidants customary or suitable for pharmaceutical applications, e.g.:

amino acids (e.g. glycine, histidine, tyrosine, tryptophan) and derivatives thereof, imidazoles (e.g. urocanic acid) and derivatives thereof, peptides such as D, L-carnosine, D-carnosine, L-camosine and derivatives thereof (e.g. anserine), carotenoids, carotenes (e.g. α-carotene, β-carotene, lycopene) and derivatives thereof, gallates (e.g. propyl gallate, dodecyl gallate, octyl gallate) and derivates thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyL methyl, ethyl, propyl, amyl, butyl and lauryl, palmitoyl, oleyl γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts), sulfoximine compounds (e.g. butbionine sulfoximines, homocysteine sulfoximine, buthionine sulfones, penta-, hexa-, heptathionine sulfoximine) in very low tolerated doses, and also (metal) chelating agents (e.g. a-hydroxy fatty acids, palmitic acid, phytic acid, lactoferrin), a-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate) and coniferyl benzoate of benzoin resin, rutinic acid and derivatives thereof, ferulic acid and derivatives thereof, butylhydroxytoluene, butylhy droxyanisole, nordihydroguaiacic acid, nordihydroguai aretic acid, trihydroxybutyrophenone, uric acid and derivatives thereof, mannose and derivatives thereof, zinc and derivatives thereof (e.g. ZnO, $ZnSO_4$), selenium and derivatives thereof (e.g. selenomethionine), stilbenes and derivatives thereof (e.g. stilbene oxide, trans-stilbene oxide) and the derivatives (salts, esters, ethers, sugars, nucleotides, nucleosides, peptides and lipids) of these listed active ingredients which are suitable according to the invention.

A further embodiment of this invention is the use of a pharmaceutical composition comprising a (crystalline) polymorph of compound of formula (I) such as FORM 1, FORM 2, FORM 3, FORM 4, FORM 5 or FORM 6 and at least one further active pharmaceutical ingredient for the treatment, diagnosis and/or prophylaxis of inflammatory diseases or conditions.

A pharmaceutical composition comprising a (crystalline) polymorph of compound of formula (I) such as FORM 1, FORM 2, FORM 3, FORM 4, FORM 5 or FORM 6 and at least one further pharmaceutically acceptable component or a pharmaceutical composition comprising a crystalline polymorph of compound of formula (I) such as FORM 1, FORM 2, FORM 3, FORM 4, FORM 5 or FORM 6 and at least one further pharmaceutically acceptable component as well as at least one further active pharmaceutical ingredient for the treatment, diagnosis, and/or prophylaxis of chronic obstructive pulmonary disease (COPD), acute lung injury (ALI), cardiopulmonary bypass, acute respiratory distress syndrome (ARDS), septic shock, sepsis, chronic inflammatory diseases such as psoriasis, atopic dermatitis, and rheumatoid arthritis, and reperfusion injury that occurs following heart attacks, strokes, atherosclerosis, and organ transplants, traumatic shock, multi-organ failure, autoimmune diseases like multiple sclerosis, percutaneous transluminal angioplasty, asthma, and inflammatory bowel diseases, Crohn's disease, and metastasis of cancers, where cell adhesion involving $sLe^a$ is involved, is also subject of the present invention.

In each case, an effective amount of the polymorphs of compound of formula (I) is administered either alone or as part of a pharmaceutically active composition to a patient in need of such treatment. It is also recognized that a combination of the crystal modifications of the compound of formula I with e.g. other anti-inflammatory drugs may be administered to a patient in need of such administration. The crystalline polymorphs of compound of formula (I) may also be administered to treat other diseases that are associated with cell-cell adhesion.

As the compound of formula (I) modulates the binding of E-selectin or P-selectin or L-selectin, any disease that is related to this interaction may potentially be treated by the modulation of this binding interaction. In addition, the crystalline polymorphs of compound of formula (I) can be used for the prophylaxis, diagnosis, and treatment of conditions where cell adhesion involving sLe$^a$, such as metastasis of certain cancers, is involved. Furthermore, the crystalline polymorphs of compound of formula (I) can be used for the treatment, diagnosis, and/or prophylaxis of diseases or conditions where selectins mediated leukocyte retention is involved, e.g. in lung diseases.

Another subject of this invention is a process for the preparation of a polymorph according to claim 1 characterized in that at least one of the following process is applied:
- a) Dissolution of compound of formula (I) in water or in an organic solvent or in a surfactant or in an ionic liquid or in a mixture of any of the aforementioned media under exposure of heat followed by precipitation or crystallization under cooling of the solution.

or
- b) Dissolution of compound of formula (I) in water or in an organic solvent or in a surfactant or in an ionic liquid or in a mixture of any of the aforementioned media under exposure of heat followed by crystallization through evaporation.

or
- c) Dissolution of compound of formula (I) in a solvent followed by fast precipitation or crystallization by addition of an anti solvent to the solution.

or
- d) Crystallization from a solution of compound of formula (I) by addition of a seed crystal.

or)
- e) Titration of compound of formula (I) with an aqueous solution of a base (e.g. sodium hydroxide, potassium hydroxide, sodium bicarbonate etc.) followed by treatment with an adsorbent agent (e.g. functionalized resin, charcoal, fused alumina etc.) followed by precipitation by addition of an aqueous solution of an acid (e.g. hydrochloric acid, sulfuric acid etc.)

or
- f) Exposure of heat and/or pressure and/or vapor to compound of formula (I).

The present invention also relates to a process for the preparation of FORM 1 of compound of formula (I) characterized in that the following process steps are applied:
- a) Add compound of formula (I) to a mixture of water and a lower alcohol (e.g. ethanol or isopropyl alcohol) in a reactor.
- b) Heat the mixture to a temperature of about 10° C. under its atmospheric boiling point and stir until dissolution.
- c) Cool the reaction mixture to a temperature between 0° C. and 25° C. and stir the reaction mixture between 0° C. and 25° C. for 30 minutes up to 20 hours.
- d) Filter the suspension.
- e) Wash the filter cake with a mixture of water and a lower alcohol (e.g. ethanol or isopropyl alcohol) previously cooled to a temperature between 0° C. and 25° C.
- f) Suspend the wet filter cake obtained from the filtration in a mixture of water and a lower alcohol (e.g. ethanol or isopropyl alcohol) in a reactor.
- g) Heat the mixture to a temperature of about 10° C. under its atmospheric boiling point and stir until dissolution.
- h) Transfer the reaction mixture from the reactor into another reactor, through a filter with a maximum porosity of 1 μm.
- i) Wash the filtration line with a mixture of water and a lower alcohol (e.g. ethanol or isopropyl alcohol) previously heated to a temperature of about 10° C. under its atmospheric boiling point.
- j) Concentrate the mixture, under vacuum.
- k) Set the solution's Karl Fischer at a value between 30% and 60%, by addition of water.
- l) Cool the reaction mixture to a temperature between 0° C. and 25° C. and stir the reaction mixture between 0° C. and 25° C. for 30 minutes up to 20 hours.
- m) Filter the suspension.
- n) Wash the filter cake with a mixture of water and a lower alcohol (e.g. ethanol or isopropyl alcohol) previously cooled to a temperature between 0° C. and 25° C.
- o) Add the filter cake from step 14 above into a reactor charged with water.
- p) Add (in relation to the amount of compound of formula (I)) at least 2 molar equivalents of a 1M aqueous solution of sodium hydroxide, prepared by dissolution of pure sodium hydroxide in water and stir the mixture until total dissolution.
- q) Add an adsorbent agent (1 to 10 molar equivalents) to the reaction mixture.
- r) Stir the reaction mixture until a purity higher than or equal to 99.0% is reached (in process control of purity by HPLC).
- s) Filter the reaction mixture, from the reactor into another reactor, R2, through a filter, F1, with a maximum porosity of 1 μm.
- t) Wash the filter cake, with water, passing the washings through F1 to R2.
- u) Charge a mixture of water and a lower alcohol (e.g. ethanol or isopropyl alcohol) into R2, through F1.
- v) Add (in relation to the amount of sodium hydroxide in step 16) an equimolar amount of a solution of hydrochloric acid.
- w) Cool the reaction mixture to a temperature between 0° C. and 25° C. and stir the reaction mixture between 0° C. and 25° C. for 30 minutes up to 20 hours.
- x) Filter the suspension.
- y) Wash the filter cake with a mixture of water and a lower alcohol (e.g. ethanol or isopropyl alcohol), previously filtered through F1.
- z) Dry the product, under vacuum, at a temperature of about 40° C. to 60° C., until water content, by Karl Fischer, is less than 3% to obtain FORM 1 of compound of formula (I).

The present invention also relates to a process for the preparation of FORM 2 of compound of formula (I) characterized, in that the following process steps are applied:
- a) Add compound of formula (I) to a mixture of water and a lower alcohol (e.g. ethanol or isopropyl alcohol) in a reactor.
- b) Heat the mixture to a temperature of about 10° C. under its atmospheric boiling point and stir until dissolution.
- c) Cool the reaction mixture to a temperature between 0° C. and 25° C. and stir the reaction mixture between 0° C. and 25° C. for 30 minutes up to 20 hours.
- d) Filter the suspension.
- e) Wash the filter cake with a mixture of water and a lower alcohol (e.g. ethanol or isopropyl alcohol) previously cooled to a temperature between 0° C. and 25° C.

f) Suspend the wet filter cake obtained from the filtration in a mixture of water and a lower alcohol (e.g. ethanol or isopropyl alcohol) in a reactor.
g) Heat the mixture to a temperature of about 10° C. under its atmospheric boiling point and stir until dissolution.
h) Transfer the reaction mixture from the reactor into another reactor, through a filter with a maximum porosity of 1 μm.
i) Wash the filtration line with a mixture of water and a lower alcohol (e.g. ethanol or isopropyl alcohol) previously heated to a temperature of about 10° C. under its atmospheric boiling point.
j) Concentrate the mixture, under vacuum.
k) Set the solution's Karl Fischer at a value between 30% and 60%, by addition of water.
l) Cool the reaction mixture to a temperature between 0° C. and 25° C. and stir the reaction mixture between 0° C. and 25° C. for 30 minutes up to 20 hours.
m) Filter the suspension.
n) Wash the filter cake with a mixture of water and a lower alcohol (e.g. ethanol or isopropyl alcohol) previously cooled to a temperature between 0° C. and 25° C.
o) Dry the product, under vacuum, at a temperature of about 40° C. to 60° C., until water content, by Karl Fischer, is less than 3% to obtain FORM 2 of compound of formula (I).

The present invention also relates to a process for the preparation of FORM 3 of compound of formula (I) characterized in that the following process steps are applied:
A) Collect and combine the filter liquor and washing solutions from the preparation of FORM 2 above in a reactor R1.
B) Concentrate the mixture, under vacuum.
C) Cool the reaction mixture to a temperature between 0° C. and 15° C. and stir the reaction mixture between 0° C. and 15° C. for up to 3 days in R1.
D) Filter the suspension.
E) Wash the filter cake with a mixture of water and a lower alcohol (e.g. ethanol or isopropyl alcohol) previously cooled to a temperature between 0° C. and 25° C.
F) Dry the product, under vacuum, at a temperature of about 40° C. to 60° C., until water content, by Karl Fischer, is less than 3% to obtain FORM 3 of compound of formula (I).

X-ray diffraction investigations of the polymorphic forms, FORM 1, FORM 2, and FORM 3 The X-ray diffraction diagrams of FORM 1, FORM 2, and FORM 3 of 1,6-Bis [3-(3-carboxymethylphenyl)-4-(2-α-D-mannopyranosyloxy)-phenyl] hexane (compound of formula (I)) according to the invention were produced from crystal powders on a Stoe Powder Diffraction System, Type P (transmission geometry) (STOE & Cie GmbH, Darmstadt, Germany) using Cu $K_{\alpha 1}$ radiation.

Below, the X-ray reflections are listed in the form that the diffraction angle 2Theta (=2Θ or 2θ) in degrees (°) is indicated at which the X-ray diffraction reflection occurs, and behind it in brackets the relative intensity of the reflection in percent of the intensity of the strongest reflection whose intensity was set equal to 100%. The relative intensities are rounded to a multiple of 0.5% of the intensity of the strongest reflection. These rounded relative intensities also form the basis for is the division into strong and medium-strong X-ray reflections carried out above and in the claims. The diffraction angles are rounded to a multiple of 0.5°.

a) X-Ray Reflections of FORM 1 of Compound of Formula (I) (2Theta [°] (Relative Intensity [%]))
4.8° (100.0%), 11.4° (4.6%), 11.6° (6.5%), 11.6° (6.5%), 11.8° (5.7%), 11.9° (5.0%), 12.1° (4.5%), 12.2° (4.1%), 12.5° (4.0%), 12.6° (3.8%), 13.1° (3.7%), 13.3° (4.2%), 13.4° (4.3%), 13.6° (4.5%), 14.0° (3.5%), 14.3° (3.5%), 14.6° (3.5%), 14.7° (3.5%), 15.1° (3.1%), 15.4° (3.5%), 15.5° (3.3%), 15.9° (3.5%), 16.4° (8.3%), 16.6° (17.7%), 16.8° (15.1%), 17.1° (4.9%), 17.3° (4.1%), 17.6° (4.5%), 17.7° (6.7%), 18.1° (4.5%), 18.1° (4.3%), 18.3° (3.7%), 19.6° (3.5%), 19.7° (3.4%), 19.8° (3.0%), 20.1° (3.8%), 20.1° (3.8%), 20.2° (3.8%), 20.6° (4.8%), 20.7° (5.8%), 20.9° (3.9%), 21.2° (3.1%), 21.6° (3.3%), 21.7° (3.3%), 21.8° (3.0%), 22.8° (4.0%), 22.9° (3.9%), 23.2° (5.3%), 23.3° (5.7%), 23.4° (5.6%), 23.8° (3.2%), 24.1° (3.8%), 24.2° (3.8%), 24.6° (7.0%), 26.0° (7.4%), 26.0° (7.0%), 26.2° (5.9%), 27.2° (2.9%), 32.9° (1.6%), 33.0° (2.1%), 33.1° (1.9%), 34.7° (2.2%), 34.8° (2.2%), 35.1° (2.3%), 35.2° (2.2%), 35.4° (2.3%), 35.5° (2.3%), 37.0° (2.5%), 37.1° (2.3%), 37.2° (1.9%), 37.8° (1.6%), 37.9° (1.60%), 42.2° (1.9%), 42.4° (2.4%), 42.5° (2.2%), 42.6° (1.9%), 48.9° (1.6%), 49.0° (1.6%), b) X-Ray Reflections of FORM 2 of Compound of Formula (I) (2Theta [°] (Relative Intensity [%]))
5.3° (55.6%), 5.6° (100.0%), 7.2° (12.8%), 9.4° (11.6%), 9.8° (11.5%), 9.9° (18.3%), 10.3° (29.0%), 10.6° (13.5%), 11.1° (9.4%), 11.7° (12.7%), 12.8° (12.4%), 13.0° (10.3%), 13.8° (40.2%), 14.6° (11.4%), 15.1° (28.9%), 15.4° (13.2%), 15.6° (13.2%), 15.8° (10.7%), 15.9° (12.3%), 16.3° (29.2%), 16.6° (42.0%), 17.0° (8.5%), 17.4° (50.9%), 17.8° (10.7%), 18.8° (47.1%), 19.1° (30.7%), 19.2° (17.6%), 19.8° (15.3%), 20.0° (14.3%), 20.1° (19.6%), 20.4° (17.2%), 20.7° (26.7%), 21.1° (8.4%), 21.5° (45.1%), 21.9° (10.5%), 22.1° (7.2%), 22.2° (10.0%), 22.6° (7.4%), 23.3° (8.7%), 23.6° (9.6%), 23.8° (7.3%), 23.9° (9.4%), 24.3° (15.2%), 24.6° (8.6%), 24.8° (19.4%), 25.0° (13.1%), 25.5° (15.7%), 25.7° (11.7%), 25.8° (9.8%), 26.3° (10.1%), 26.5° (22.0%), 26.8° (9.0%), 27.0° (8.3%), 27.2° (6.3%), 27.4° (7.0%), 27.7° (8.4%), 27.9° (8.5%), 28.3° (7.7%), 28.7° (7.1%), 28.9° (5.1%), 29.7° (5.1%), 30.2° (6.1%), 30.8° (5.5%), 31.2° (5.2%), 31.8° (6.0%), 32.2° (9.2%), 32.4° (3.9%), 32.5° (4.0%), 3.6° (5.9%), 34.0° (6.0%), 34.3° (5.3%), 34.8° (4.3%), 34.8° (3.6%), 35.2° (6.7%), 35.5° (4.7%), 35.8° (4.6%), 36.2° (4.5%), 36.4° (5.2%), 36.8° 3.9%), 37.0° (4.8%), 37.4° (7.5%), 37.7° (9.7%), 37.8° (6.8%), 38.1° (4.9%), 38.4° (4.9%), 38.7° (4.2%), 38.9° (6.1%), 39.1° (5.0%), 39.8° (6.0%), 40.1° (4.1%), 40.2° (4.2%), 40.6° (5.9%), 40.7° (5.2%), 41.4° (4.6%), 42.0° (4.3%), 42.6° (3.9%), 43.6° (4.0%), 43.8° (3.4%), 44.4° (4.6%), 44.8° (3.2%), 45.2° (3.1%), 46.2° (3.1%), 46.6° (2.9%), 47.0° (2.6%), 47.8° (3.3%), 48.1° (3.4%), 48.5° (3.7%), 48.7° (3.4%), 49.0° (4.0%).

c) X-Ray Reflections of FORM 3 of Compound of Formula (I) (2Theta [° ] (Relative Intensity [%]))
4.2° (17.6%), 4.3° (20.6%), 4.8° (29.1%), 5.3° (56.0%), 5.6° (100.0%), 7.3° (15.3%), 9.4° (14.3%), 9.9° (20.6%), 10.3° (30.7%), 10.6° (16.4%), 11.7° (17.7%), 12.8° (14.4%), 12.9° (13.4%), 13.8° (37.9%), 14.1° (11.0%), 14.6° (13.4%), 15.1° (29.1%), 15.4° (14.5%), 15.7° (14.4%), 15.9° (14.3%), 16.3° (30.4%), 16.6° (44.4%), 16.9° (15.8%), 17.4° (48.6%), 17.8° (13.6%), 18.8° (46.0%), 19.1° (32.0%), 19.3° (18.9%), 19.8° (17.4%), 20.0° (17.9%), 20.1° (21.7%), 20.4° (18.5%), 20.7° (29.1%), 20.9° (8.6%), 21.1° (10.3%), 21.6° (47.7%), 21.9° (12.4%), 22.2° (11.3%), 22.6° (9.1%), 22.7° (9.2%), 22.9° (7.5%), 23.3° (10.8%), 23.5° (11.1%), 23.9° (11.2%), 24.3 (16.3%), 24.4° (10.4%), 24.8° (20.2%), 25.0° (14.3%), 25.5° (17.0%), 25.7° (13.0%), 25.9° (11.0%), 26.3° (12.8%), 26.5°

(25.1%), 26.7° (10.3%), 26.8° (10.6%), 27.0° (10.4%), 27.2° (7.8%), 27.4° (8.5%), 27.7° (9.8%), 27.9° (9.6%), 28.3° (9.0%), 28.7° (8.0%), 28.9° (6.2%), 29.1° (5.4%), 29.3° (5.2%), 29.7° (5.9%), 29.8° (6.1%), 30.2° (7.1%), 30.6° (4.6%), 30.8° (6.4%), 31.1° (5.9%), 31.6° (5.5%), 31.8° (7.1%), 32.2° (9.9%), 32.5° (5.0%), 33.0° (4.7%), 33.6° (6.7%), 33.7° (5.8%), 34.0° (6.6%), 34.3° (6.2%), 34.8° (5.2%), 34.8° (5.1%), 35.1° (5.5%), 35.2° (7.7%), 35.5° (5.9%), 35.7° (5.4%), 35.8° (5.8%), 36.3° (5.8%), 36.4° (5.8%), 36.7° (4.8%), 37.0° (5.8%), 37.1° (5.4%), 37.4° (8.2%), 37.7° (10.4%), 37.8° (10.1%), 38.1° (5.6%), 38.3° (5.8%), 38.5° (4.7%), 38.7° (4.9%), 38.8° (7.0%), 39.1° (5.6%), 39.8° (6.5%).

X-ray diffraction investigations of the polymorphic forms, FORM 4, FORM 5, and FORM 6 The X-ray diffraction diagrams of FORM 4, FORM 5 and FORM 6 of 1,6-Bis [3-(3-carboxymethylphenyl)-4-(2-α-D-mannopyranosyloxy)-phenyl] hexane (compound of formula (I)) according to the invention were collected on a Siemens D5000 diffractometer using Cu K$_{α1}$ radiation (40 kV, 40 mA), Θ-Θ goniometer, V20 variable divergence and receiving slits, a graphite secondary monochromator and scintillation counter.

Below, the X-ray reflections are listed in the form that the diffraction angle 2Theta (=2Θ or 2θ) in degrees (°) is indicated at which the X-ray diffraction reflection occurs, and behind it in brackets the relative intensity of the reflection in percent of the intensity of the strongest reflection whose intensity was set equal to 100%. The relative intensities are rounded to a multiple of 0.5% of the intensity of the strongest reflection. These rounded relative intensities also form the basis for is the division into strong and medium-strong X-ray reflections carried out above and in the claims. The diffraction angles are rounded to a multiple of 0.5°.

a) X-Ray Reflections of FORM 4 of Compound of Formula (I) (2Theta [°] (Relative Intensity [%]))
4.1° (17.3%), 4.2° (42.1%), 4.3° (52.9%), 4.4° (44.3%), 4.5° (21.2%), 4.6° (12.3%), 4.7° (10.5%), 4.8° (9.7%), 8.4° (9.7%), 8.5° (11.6%), 8.6° (7.3%), 11.4° (10.4%), 11.5° (19.7%), 11.6° (28.6%), 11.7° (31.2%), 11.8° (27.3%), 11.9° (24.1%), 12.0° (16.7%), 12.1° (13.4%), 12.2° (13.0%), 12.3° (11.0%), 12.4° (9.7%), 12.5° (8.9%), 16.1° (10.9%), 16.2° (14.1%), 16.3° (21.1%), 16.4° (36.9%), 16.5° (58.1%), 16.6° (79.9%), 16.7° (95.9%), 16.8° (100.0%), 16.9° (92.0%), 17.0° (70.2%), 17.1° (47.1%), 17.2° (31.5%), 17.3° (22.3%), 17.4° (17.3%), 17.7° (15.7%), 17.8° (20.8%), 17.9° (23.5%), 18.0° (26.2%), 18.1° (27.6%), 18.2° (29.5%), 18.3° (26.0%), 18.4° (20.6%), 19.0° (21.3%), 19.1° (25.4%), 19.2° (28.6%), 19.3° (31.3%), 19.4° (34.5%), 19.5° (38.0%), 19.6° (40.2%), 19.7° (43.4%), 19.8° (42.5%), 19.9° (40.0%), 20.0° (37.7%), 20.1° (31.4%), 20.2° (26.7%), 21.2° (26.3%), 21.3° (31.9%), 21.4° (33.4%), 21.5° (37.0%), 21.6° (34.4%), 21.7° (28.9%), 21.8° (23.9%), 25.4° (24.5%), 25.5° (24.6%), 25.6° (26.2%), 25.7° (28.0%), 25.8° (31.4%), 25.9° (34.1%), 26.0° (40.7%), 26.1° (45.2%), 26.2° (50.9%), 26.3° (56.4%), 26.4° (62.5%), 26.5° (64.2%), 26.6° (60.2%), 26.7° (54.2%), 26.8° 46.5%), 26.9° (38.6%), 27.0° (33.7%), 27.1° (31.3%), 27.2° (29.5%), 27.3° (25.5%), 27.4° 23.0%), 27.5° (21.4%).

b) X-Ray Reflections of FORM 5 of Compound of Formula (I) (2Theta [°] (Relative Intensity [%]))
5.0° (7.5%), 5.1° (33.1%), 5.2° (68.2%), 5.3° (63.0%), 5.4° (32.0%), 5.5° (66.6%), 5.6° (70.4%), 5.7° (32.5%), 9.2° (6.9%), 9.3° (8.3%), 9.4° (5.6%), 9.7° (7.0%), 9.8° (12.0%), 9.9° (13.2%), 10.0° (10.6%), 10.1° (22.2%), 10.2° (28.2%), 10.3° (21.7%), 10.4° (14.7%), 10.5° (17.4%), 10.6° (12.2%), 10.7° (6.1%), 11.4° (5.3%), 11.5° (9.9%), 11.6° (14.4%), 11.7° (13.0%), 11.8° (6.8%), 12.6° (6.5%), 12.7° (6.3%), 13.6° (9.7%), 13.7° (13.6%), 13.8° (12.8%), 14.4° (12.4%), 14.5° (14.8%), 14.6√ (9.9%), 14.9° (13.9%), 15.0° (17.0%), 15.1° (14.1%), 15.6° (10.1%), 15.7° (18.4%), 15.8° (24.3%), 15.9° (21.6%), 16.0° (13.7%), 16.1° (13.8%), 16.2° (17.4%), 16.3° (22.8%), 16.4° (36.7%), 16.5° (45.7%), 16.6° (40.7%), 16.7° (24.6%), 16.8° (12.9%), 17.0° (11.5%), 17.1° (20.6%), 17.2° 31.0%), 17.3° (33.1%), 17.4° (23.2%), 17.5° (15.1%), 18.4° (15.8%), 18.5° (30.2%), 18.6° 45.4%), 18.7° (47.4%), 18.8° (36.8%), 18.9° (29.8%), 19.0° (28.2%), 19.1° (25.6%), 19.2° (19.2%), 19.3° (13.7%), 19.5° (12.5%), 19.6° (17.7%), 19.7° (28.7%), 19.8° (37.8%), 19.9° (47.0%), 20.0° (49.5%), 20.1° (43.9%), 20.2° (34.5%), 20.3° (31.2%), 20.4° 39.4%), 20.5° (46.5%), 20.6° (47.0%), 20.7° (35.6%), 21.0° (24.0%), 21.1° (28.0%), 21.2° 48.8%), 21.3° (85.8%), 21.4° (100.0%), 21.5° (90.4%), 21.6° (54.2%), 21.7° (32.5%), 21.8° (28.5%), 21.9° (26.7%), 22.0° (22.1%), 22.1° (18.7%), 22.2° (17.5%), 22.3° (14.6%), 22.4° (13.9%), 22.5° (14.6%), 22.6° (12.6%), 22.7° (11.0%), 22.8° (10.4%), 23.0° (13.3%), 23.1° (17.3%), 23.2° (22.6%), 23.3° (29.3%), 23.4° (31.1%), 23.5° (29.2%), 23.6° (23.9%), 23.7° (23.7%), 23.8° (23.0%), 24.3° (20.6%), 24.4° (22.2%), 24.5° (22.4%), 24.6° (22.9%), 24.7° (22.9%), 24.8° (24.0%), 24.9° (20.9%), 25.4° (16.3%), 25.5° (17.1%), 25.6° (16.5%), 26.0° (19.5%), 26.1° (25.5%), 26.2° (29.5%), 26.3° (30.0%), 26.4° (24.1%), 26.6° (21.8%), 27.1° (20.2%), 27.2° (21.4%), 27.3° (21.0%), 27.4° (18.4%), 27.5° (15.9%), 27.6° (12.6%), 27.7° (12.6%), 28.1° (12.9%), 28.2° (14.0%), 28.3° (14.9%), 28.4° (14.6%), 28.5° (14.2%), 28.7° (11.8%), 29.4° (8.7%), 29.5° (9.5%), 29.6° (8.2%).

c) No crystalline solid was observed. X-ray diffraction diagram of FORM 6 of compound of formula (I) shows a broad peak (2Theta) at 19.6°.

ATR-FT-IR Investigations of the Polymorphic Forms

The IR spectra of FORM 1, FORM 2 and FORM 3 of 1,6-Bis [3-(3-carboxymethylphenyl)-4-(2-α-D-mannopyranosyloxy)-phenyl] hexane (compound of formula (I)) according to the invention were produced from an attenuated total reflectance Fourier transform infra red spectrometer Spectrum One (Perkin Elmer Instruments GmbH, Rodgau-Juegesheim, Germany). For IR measurement 5 mg of solid sample were placed on the top of the ATR probe head and slightly pressed by the adjusting screw onto the diamond window of the probe head. Below, the IR bands are listed within a range of 4000 cm$^{-1}$ and 550 cm$^{-1}$ in the form that the wave numbers are indicated at which an IR transmission occurs, and behind it in brackets the relative intensity of the transmission in percent compared to total transmission (100%). The relative intensities are rounded to a multiple of 0.1%. A threshold of 2% is applied; 4 IR scans were applied per run. The wave numbers are rounded to a multiple of 1 cm$^{-1}$.

a) Main Wave Numbers of FORM 1 of Compound of Formula (I) (ν [cm$^{-1}$] (Relative Intensity [%]))
3404 (64.5), 2931 (64.0), 1707 (41.3), 1608 (70.0), 1500 (62.0), 1479 (61.6), 1445 (66.3), 1435 (66.7), 1400 (62.9), 1358 (67.0), 1272 (60.0), 1245 (53.8), 1228 (52.5), 1166 (70.1), 1136 (49.1), 1095 (57.4), 1050 (44.3), 1004 (54.5), 977 (39.8), 930 (67.3), 915 (66.2), 900 (65.3), 854 (69.2), 828 (63.8), 818 (52.8), 801 (58.0), 770 (69.8), 725 (68.8), 706 (61.4), 690 (57.1), 615 (60.1), 602 (67.0), 595 (68.5), 591 (64.7), 586 (61.0), 579 (67.4), 573 (64.0), 568 (70.3), 563 (69.5), 557 (72.6).

b) Main Wave Numbers of FORM 2 of Compound of Formula (I) (ν [cm$^{-1}$] (Relative Intensity [%]))
3246 (67.2), 2933 (71.8), 2857 (75.1), 1728 (57.3), 1601 (75.4), 1499 (67.4), 1478 (62.8), 1459 (69.9), 1402 (73.0), 1323 (73.1), 1226 (46.5), 1148 (69.4), 1119 (55.4), 1096 (59.6), 1077 (56.4), 1066 (44.0), 1048 (51.8), 1017 (31.2), 997 (52.7), 982 (45.7), 920 (73.7), 899 (75.4), 875 (73.4), 843 (67.1), 826 (68.9), 817 (71.2), 800 (52.7), 785 (74.4), 759

(77.0), 747 (73.6), 720 (66.3), 704 (62.6), 686 (53.6), 660 (65.2), 640 (66.9), 627 (70.4), 605 (55.1), 580 (74.9), 575 (78.5), 568 (73.3), 561 (77.4), 555 (76.2).

c) Main Wave Numbers of FORM 6 of Compound of Formula (I) (v [cm$^{-1}$] (Relative Intensity [%]))
3387 (88.6%), 2928 (87.5%), 2855 (91.4%), 1710 (82.4%), 1607 (94.0%), 1500 (87.9%), 1478 (85.9%), 1367 (88.0%), 1223 (73.8%), 1115 (74.8%), 1065 (73.6%), 1048 (75.9%), 1010 (64.5%), 977 (68.0%), 908 (84.0%), 890 (82.7%), 848 (85.1%), 821 (81.2%), 797 (79.1%), 779 (84.6%), 771 (86.0%), 762 (86.7%), 752 (86.0%), 745 (85.5%), 736 (85.5%), 727 (84.1%), 719 (84.2%), 703 (75.1%), 685 (77.0%), 677 (77.5%), 668 (78.8%), 659 (80.5%).

Thermodynamic Solubility Investigations with the Polymorphic Forms in Organic Solvents The thermodynamic solubility of FORM 1, FORM 2, FORM 4, and FORM 6 of 1,6-Bis [3-(3-carboxymethylphenyl)-4-(2-α-D-mannopyranosyloxy)-phenyl] hexane (compound of formula (I)) was determined in several organic solvents by suspending sufficient compound to give a maximum final concentration. Quantification was by reverse phase HPLC with gradient solution with reference to a standard solution of FORM B of the compound of formula (I) at 0.25 mg/ml. The suspensions were equilibrated at 27° C. for 24 hours with shaking. All suspensions were filtered though a glass fibre C filter. The filtrate was then diluted by an appropriate factor in 50:50 ethanol:water apart from isopropyl myristate which was diluted in ethanol to avoid emulsion formation.

Solubilities were calculated using the peak areas determined by the peak found at the same retention time as the principal peak in the standard injection. The following Table summarizes the results:

TABLE

| EtOH | | IPA | | Triacetin | | Propylene Glycol | | PEG 300 | |
|---|---|---|---|---|---|---|---|---|---|
| FORM | mg/ml | FORM | mg/ml | FORM | mg/ml | FORM | mg/ml | FORM | mg/ml |
| 4 | 48 | 6 | 27 | 1 | 0.056 | 1 | 199 | 1 | 205 |
| 6 | 20 | 1 | 3.9 | 4 | 0.02 | 6 | 170 | 4 | 159 |
| 1 | 4.2 | 4 | 1.2 | 2 | 0.0083 | 4 | 165 | 6 | 122 |
| 2 | 4.2 | 2 | 0.52 | 6 | N/A | 2 | 104 | 2 | 102 | mg/ml: Solubility in mg/ml;
N/A not available;
EtOH: Ethanol;
IPA: Isopropyl alcohol;
Triacetin: glycerin triacetate;
PEG 300: Polyethylene glycol 300.

FORM 4 has highest solubility in ethanol, FORM 6 in IPA, and FORM 1 in Triacetin, propylene glycol, and PEG 300. Polymorphic conversions in the various solvents may, at least in part, impact the solubility values obtained in this study.

Thermodynamic Solubility Investigations with the Polymorphic Forms in Water

The thermodynamic solubility of FORM 1, FORM 2, and FORM 3 of 1,6-Bis [3-(3-carboxymethylphenyl)-4-(2-α-D-mannopyranosyloxy)-phenyl] hexane (compound of formula (I)) was determined in water by employing the shake flask technique. The sample was added to pure water in a Safelock-tube (Eppendorf, Germany) under vigorous shaking until a white precipitate was formed. The saturated solution was incubated over night at 25° C. in an Eppendorf Thermomixer operated at 700 RPM. The suspension was cleared by centrifugation at 13.000 RPM at room temperature, and the supernatant was carefully collected. The supernatant was further purified by vacuum-filtration through a Millipore solubility filter plate (Millipore, Molsheim, France).

The UV absorption of the filtrate was measured against pure water using a Spectramax250 (Molecular Devices, Sunnyvale, Calif.) operated with Softmax Pro v. 4.8 software, using the application "Mscreen solubility quantify" in the ADME package. The sample concentration was calculated using a 5-point linear calibration line of the compound of formula (I) in acetonitrile:pure water (1:1 vol:vol). Measurements have been performed in triplicate.

The following solubilities in mg/L obtained are shown in the Table:

TABLE

| FORM 1: | 22 mg/L |
|---|---|
| FORM 2: | 15 mg/L |
| FORM 3: | 14 mg/L |

Differential Scanning Calorimetry (DSC)

DSC data for FORM 1, FORM 2, FORM 3, FORM 4, FORM 5, and FORM 6 of 1,6-Bis [3-(3-carboxymethylphenyl)-4-(2-α-D-mannopyranosyloxy)-phenyl] hexane (compound of formula (I)) were collected on a TA Instruments Q1000 equipped with a 50 position autosampler. The instrument was calibrated for energy and temperature calibration using certified indium. Typically 0.5-3 mg of each sample, in a pin-holed aluminum pan, was heated at 10° C./min. from 25° C. to 235° C. A nitrogen purge at 30 ml/min. was maintained over the sample.

a) FORM 1 of Compound of Formula (I)

A single endotherm peak with onset at 136° C. was observed (FIG. 7).

b) FORM 2 of Compound of Formula (I)

A shallow endotherm peak at ca. 75° C. and an endotherm peak with onset at 158° C. was observed (FIG. 8).

e) FORM 3 of Compound of Formula (I)

Three endotherm peaks were observed. The first peak occurs at approximately 74° C., followed by two peaks with onset at 138° and 158° C. (see FIG. 9).

d) FORM 4 of Compound of Formula (I)

Two endotherm peaks were observed, one with onset at 39° C. followed by the melt at 132° C. (FIG. 10).

e)

f) FORM 5 of Compound of Formula (I)

Thermal analysis showed a single melt onset at 158° C. (FIG. 11).

f) FORM 6 of Compound of Formula (I)

Thermal analysis showed a broad endotherm peak at 40-80° C. (FIG. 12).

Thermo-Gravimetric Analysis (TGA)

TGA data were collected for FORM 1, FORM 2, FORM 3, FORM 4, and FORM 6 of 1,6-Bis [3-(3-carboxymethylphenyl)-4-(2-α-D-mannopyranosyloxy)-phenyl] hexane (compound of formula (I)) on a TA Instruments Q500 TGA, equipped with a 16 position autosampler. The instrument was temperature calibrated using certified Alumel. Typically 5-30 mg of each sample was loaded onto a pre-tared platinum crucible and aluminum DSC pan, wad was heated at 10° C./min from ambient temperature to 350° C. A nitrogen purge at 60 ml/min was maintained over the sample.

a) FORM 1 of Compound of Formula (I)

The thermal analysis of FORM 1 showed no weight loss prior to degradation at high temperatures (FIG. 13).

b) FORM 2 of Compound of Formula (I)

Thermal analysis of FORM 2 showed the material was solvated as there was a weight loss of 2.1% at about 75° C. (FIG. 14).

c) FORM 3 of Compound of Formula (I)

Thermal analysis of FORM 3 showed the material was solvated as there was a weight loss of 1.8% at about 57° C. (FIG. 15).

d) FORM 4 of Compound of Formula (I)

Thermal analysis of FORM 4 suggested that FORM 4 is a hydrate as the TGA thermogram showed a weight loss of 6.2% which represents ca. 3 molecules of water (5.9% theoretical value) indicating a trihydrate (FIG. 16). This assumption is supported by the results of the Karl Fischer titration.

e) FORM 6 of Compound of Formula (I)

Thermal analysis suggested that FORM 6 is a solvate as there was a weight loss of about 2.9% between 32-71° C. A second weight loss of about 2.3% between 70-110° C. is observed. (FIG. 17).

Water Determination by Karl Fischer

The content of water of FORM 2 and FORM 4 of 1,6-Bis [3-(3-carboxymethylphenyl)-4-(2-α-D-mannopyranosyloxy)-phenyl] hexane (compound of formula (1)) was determined by employing the Karl Fischer method on a Mettler Toledo DL39 Coulometer using Hydranal Coulomat AG reagent and an argon purge. Weighed solid samples were introduced into the vessel on a platinum TGA pan which was connected to a subseal to avoid water ingress. Approximately 10 mg of sample was used per titration and duplicate determinants were made.

a) FORM 2 of Compound of Formula (I)

A water content of 2.2% was observed. Taking the results of the TGA and DSC analysis into account, FORM 2 is considered to represent a monohydrate of the compound of formula (I).

b) FORM 4 of Compound of Formula (I)

A water content of 6.9% was observed. Taking the results of the TGA and DSC analysis into account, FORM 2 is considered to represent a trihydrate of the compound of formula (I).

Melting Points of the Polymorphic Forms

A capillary melting point was determined for FORM 1, FORM 2, and FORM 3 of 1,6-Bis [3-(3-carboxymethylphenyl)-4-(2-α-D-mannopyranosyloxy)-phenyl] hexane (compound of formula (I)) using standard methods known to the person skilled in the art.

The melting points of FORM 4, FORM 5 of 1,6-Bis [3-(3-carboxymethylphenyl)-4-(2-α-D-mannopyranosyloxy)-phenyl] hexane (compound of formula (I)) were determined by the DSC method.

a) FORM 1 of Compound of Formula (I)

On average, FORM 1 of compound of formula (I) shows melting in the following temperature range: 134° C.-139° C.

b) FORM 2 of Compound of Formula (I)

On average, FORM 2 of compound of formula (I) shows melting in the following temperature range: 158° C.-161° C.

c) FORM 3 of Compound of Formula (I)

On average, FORM 3 of compound of formula (I) shows melting in the following temperature range: 161° C.-165° C.

d) FORM 4 of Compound of Formula (I)

After loss of water FORM 4 melted at 132° C. In order to prevent loosing water before melting, the DSC experiment was conducted in a hermetic pan. A melting point of FORM 4 at 86° C. was determined.

e) FORM 5 of Compound of Formula (I)

FORM 5 of compound of formula (I) shows melting at 158° C.

Other features of the invention will become apparent in the course of the following descriptions of exemplary embodiments, which are given for illustration of the invention.

In the Figures enclosed to this application describe the crystalline modifications more in detail.

FIG. 17 shows the results of a Thermo-Gravimetric Analysis (TGA) of Form 6.

Example 1

Figure 1:
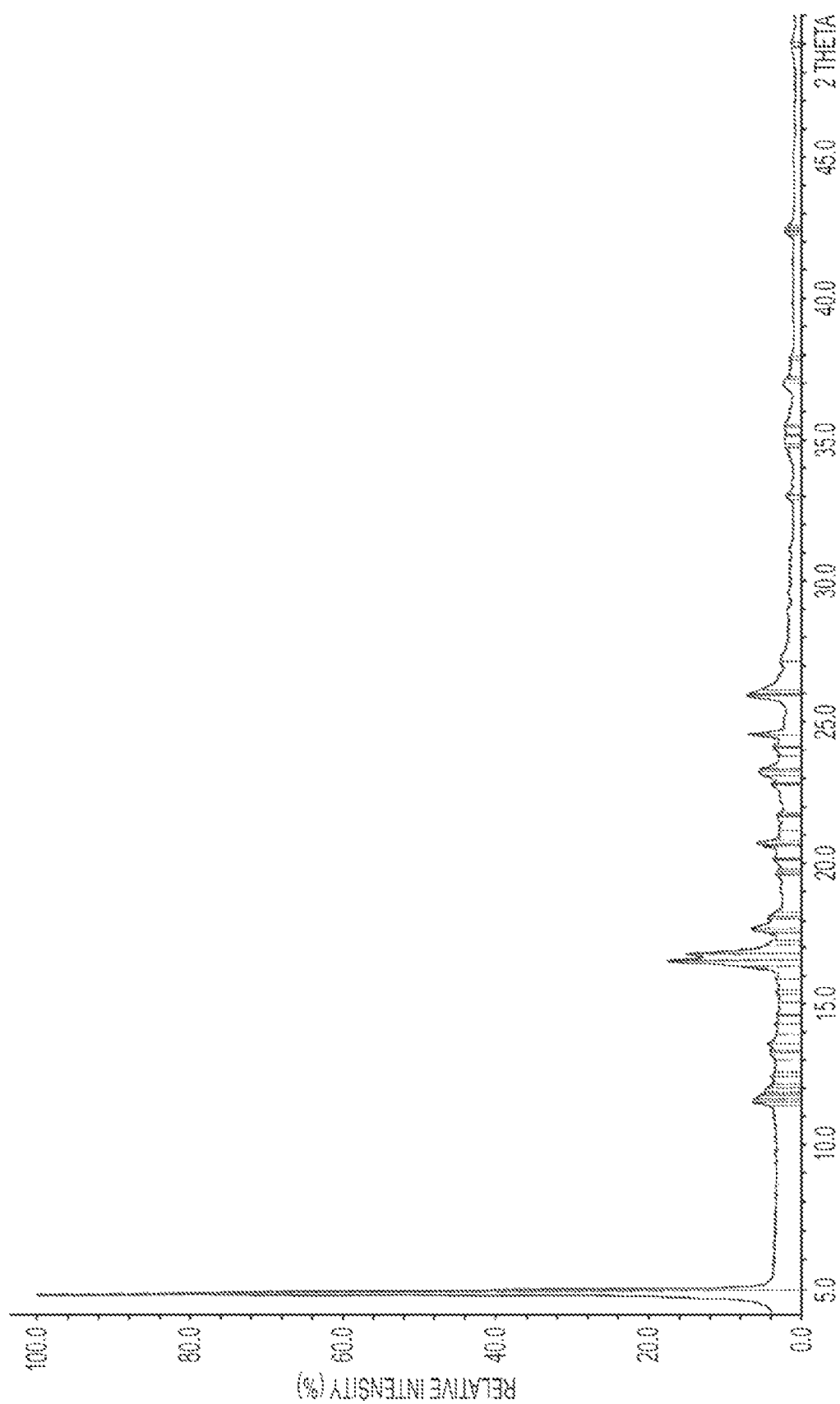
FIG. 1 shows the crystalline modification of Form 1 with the Relative Intensity (in %) shown as a function of 2Theta.

Generation of FORM 1 of Compound of Formula (I)

The following process steps are applied:
1. Charge isopropyl alcohol and water into a reactor, R1.
2. Add, with stirring, compound of formula (I).
3. Heat the reaction mixture to about 45° C. to 60° C.
4. Stir the reaction mixture at about 45° C. to 60° C. until dissolution.

5. Cool the reaction mixture to 10° C./20° C. for at least 60 to 120 minutes.
6. Stir the reaction mixture. at 15° C./20° C. for at least 90 to 150 minutes.
7. Filter the suspension.
8. Wash the filter cake twice with a mixture of isopropyl alcohol and water, previously cooled to a temperature between 20° C. and 10° C.
9. Charge isopropyl alcohol and water into R1.
10. Suspend the wet product, obtained from the filtration, in R1.
11. Heat the reaction mixture to about 45° C. to 60° C.
12. Stir the reaction mixture at about 45° C. to 60° C. until dissolution.
13. Transfer the reaction mixture from R1 to a reactor, R2, through a filter with a maximum porosity of 1 μm.
14. Wash the filtration line with a mixture of isopropyl alcohol and water, previously heated to about 45° C. to 60° C.
15. Concentrate the reaction mixture, under vacuum.
16. Set the solution's Karl Fischer at a value of 40% to 50%, by addition of water.
17. Cool the reaction mixture to 10° C./20° C. for at least 60 to 120 minutes.
18. Stir the reaction mixture at 10° C./20° C. for at least 90 to 150 minutes.
19. Filter the suspension.
20. Wash the filter cake twice with a mixture of isopropyl alcohol and water, previously cooled to a temperature between 10° C. and 20° C.
21. Dry the product, under vacuum, at a temperature of about 50° C., until water content, by Karl Fischer, is less than 1.5%.

With the above procedure compound of formula I is obtained with a HPLC measured purity of more than 80%.

1. Charge water into a reactor, R1.
2. Add, with stirring, dried product from step 21 above.
3. Add (in relation to the amount of compound of formula (I)) at least 2 molar equivalents of a 1M aqueous solution of sodium hydroxide, prepared by dissolution of pure sodium hydroxide in water.
4. Stir the reaction mixture until total dissolution.
5. Add resin type D (XAD 16) (50 wt % in relation to the amount of compound of formula (I)) to the contents of R1.
6. Stir the reaction mixture for at least 2 hours. Take samples for in process control by HPLC (purity higher than or equal to 99.0%).
7. Filter the reaction mixture, from R1 to a reactor, R2, through a filter, F1, with a maximum porosity of 1 μm.
8. Wash the filter cake twice, with water, passing the washings through F1 to R2.
9. Charge isopropyl alcohol into R2, through F1.
10. Add (in relation to the amount of sodium hydroxide in step 3 above) an equimolar amount of a 1M solution of hydrochloric acid, prepared by dissolution of hydrochloric acid in water, through F1.
11. Cool the reaction mixture to 0° C./10° C. (crystallization occurs).
12. Stir the reaction mixture at 0° C./10° C., for at least 2 hours to 5 hours.
13. Filter the suspension.
14. Wash the filter cake twice with a mixture of isopropyl alcohol and water, previously filtered through F1.
15. Dry the product, under vacuum, at a temperature of about 50° C., until water content, by Karl Fischer, is less than 1.5%.

With the above procedure compound of formula (I) is obtained in more than 70% (w/w) yield with a HPLC measured purity of more than 99.0% and in crystal modification Form 1.

Example 2

Generation of FORM 2 of Compound of Formula (I)

The following process steps are applied:
1. Charge isopropyl alcohol and water into a reactor, R1.
2. Add, with stirring, compound of formula (I).
3. Heat the reaction mixture to about 45° C. to 60° C.
4. Stir the reaction mixture at about 45° C. to 60° C. until dissolution.
5. Cool the reaction mixture to 10° C./20° C. for at least 60 to 120 minutes.
6. Stir the reaction mixture at 15° C./20° C. for at least 90 to 150 minutes.
7. Filter the suspension.
8. Wash the filter cake twice with a mixture of isopropyl alcohol and water, previously cooled to a temperature between 20° C. and 10° C.
9. Charge isopropyl alcohol and water into R1.
10. Suspend the wet product, obtained from the filtration, in R1.
11. Heat the reaction mixture to about 45° C. to 60° C.
12. Stir the reaction mixture at about 45° C. to 60° C. until dissolution.
13. Transfer the reaction mixture from R1 to a reactor, R2, through a filter with a maximum porosity of 1 μm.
14. Wash the filtration line with a mixture of isopropyl alcohol and water, previously heated to about 45° C. to 60° C.
15. Concentrate the reaction mixture, under vacuum.
16. Set the solution's Karl Fischer at a value of 40% to 50%, by addition of water.
17. Cool the reaction mixture to 10° C./20° C. for at least 60 to 120 minutes.
18. Stir the reaction mixture at 10° C./20° C. for at least 90 to 150 minutes.
19. Filter the suspension.
20. Wash the filter cake twice with a mixture of isopropyl alcohol and water, previously cooled to a temperature between 10° C. and 20° C.
21. Dry the product, under vacuum, at a temperature of about 50° C., until water content, by Karl Fischer, is less than 1.5%.

With the above procedure compound of formula (I) is obtained in more than 70% (w/w) yield with a HPLC measured purity of more than 99.0% and in crystal modification Form 2.

Example 3

Generation of FORM 3 of Compound of Formula (I)

The following process steps are applied:
1. Collect and combine the filter liquor and washing solutions from the generation of FORM 2 (see above) in a reactor, R1.
2. Concentrate the mixture, under vacuum.
3. Cool the reaction mixture to a temperature between 0° C. and 10° C. and stir the reaction mixture between 0° C. and 10° C. for 36 hours in R1.
4. Filter the suspension.

5. Wash the filter cake triple with a mixture of water and isopropyl alcohol, previously cooled to a temperature between 0° C. and 10° C.
6. Dry the product, under vacuum, at a temperature of about 50° C., until water content, by Karl Fischer, is less than 2%.

With the above procedure compound of formula (I) is obtained in more than 70% (w/w) yield with a HPLC measured purity of more than 98.0% and in crystal modification Form 3.

Example 4

Generation of FORM 1 of Compound of Formula (I)

FORM 1 of 1,6-Bis [3-(3-carboxymethylphenyl)-4-α-D-mannopyranosyloxy)-phenyl] hexane (compound of formula (I)) was prepared by desolvation of FORM 4 according to the methods known to the person skilled in the art at 86° C.

Example 5

Generation of FORM 2 of Compound of Formula (I)

FORM 2 of 1,6-Bis [3-(3-carboxymethylphenyl)-4-(2-α-D-mannopyranosyloxy)-phenyl] hexane (compound of formula (I)) was prepared according to the methods principally known to the person skilled in the art by preparing slurries of FORM 6 in a ratio 30 mg of compound of formula (I) in 0.2 ml solvent at room temperature, prior to warming the sample to 50° C. Samples which formed slurries were matured for four days on 4 hour a heat/cool between room temperature and 50° C. Solutions Which were formed at 50° C. were initially cooled to room temperature followed by evaporation to dryness at room temperature.

Here, the following solvents can be used to prepare FORM 1: Dioxane, Diethyl ether, Ethyl acetate, IPA (isopropyl alcohol), THF (tetrahydrofuran), DCM (dichloromethane), MIBK (methyl isobutyl ketone), MEK (methyl ethyl ketone), n-Propanol, Ethanol, Methanol, 50% aq. Ethanol.

Example 6

Generation of FORM 2 of Compound of Formula (I)

FORM 2 of 1,6-Bis [3-(3-carboxymethylphenyl)-4-(2-α-D-mannopyranosyloxy)-phenyl] hexane (compound of formula (I)) was prepared according to the methods known to the person skilled in the art by storing FORM 5 at 40° C. and 75% relative humidity for 1 day.

Example 7

Generation of FORM 2 of Compound of Formula (I)

FORM 2 of 1,6-Bis [3-(3-carboxymethylphenyl)-4-(2-α-D-mannopyranosyloxy)-phenyl] hexane (compound of formula (I)), FORM 6, is prepared according to the methods known to the person skilled in the art by slurrying FORM 4 and/or FORM 5 in either 5% or 50% aq. Isopropyl acetate (IPAc) at 40° C. or more or by slurrying FORM 4 and/or FORM 5 in 10% aq. Isopropyl acetate (IPAc) at more than 40° C.

Example 8

Generation of FORM 3 of Compound of Formula (I)

FORM 3 of 1,6-Bis [3-(3-carboxymethylphenyl)-4-α-D-mannopyranosyloxy)-phenyl] hexane (compound of formula (I)) was prepared according to the methods known to the person skilled in the art by preparing slurries of FORM 6 in a ratio 30 mg of compound of formula (I) in 0.2 ml solvent at room temperature, prior to warming the sample to 50° C. Samples which formed slurries were matured for four days on 4 hour a heat/cool between room temperature and 50° C. Solutions which were formed at 50° C. were initially cooled to room temperature followed by evaporation to dryness at room temperature.

Here, the following solvents can be used to prepare FORM 3: MeCN (methyl cyanide, acetonitrile), acetone, 1-butanol, ethyl formate, IPAc (isopropyl acetate), or MTBA (tertiary butyl methyl ether).

Example 9

Generation of FORM 4 of Compound of Formula (I)

FORM 4 of 1,6-Bis [3-(3-carboxymethylphenyl)-4-(2-α-D-mannopyranosyloxy)-phenyl] hexane (compound of formula (I)) was prepared according to the methods known to the person skilled in the art by preparing slurries of FORM 6 in a ratio 30 mg of compound of formula (I) in 0.2 ml 50% aq. TPA or water at room temperature, prior to warming the sample to 50° C. Samples which formed slurries were matured for four days on 4 hour a heat/cool between room temperature and 50° C. Solutions which were formed at 50° C. were initially cooled to room temperature followed by evaporation to dryness at room temperature.

Example 10

Generation of FORM 4 of Compound of Formula (I)

FORM 4 of 1,6-Bis [3-(3-carboxymethylphenyl)-4-(2-α-D-mannopyranosyloxy)-phenyl] hexane (compound of formula (I)) was prepared according to the methods known to the person skilled in the art by storing FORM 1 at 40° C. and 75% relative humidity.

Example 11

Generation of FORM 5 of Compound of Formula (I)

FORM 5 of 1,6-Bis [3-(3-carboxymethylphenyl)-4-(2-α-D-mannopyranosyloxy)-phenyl] hexane (compound of formula (I)) was prepared according to the methods known to the person skilled in the art by desolvation of FORM 2 at 100° C.

Example 12

Generation of FORM 6 of Compound of Formula (I)

The amorphous form of 1,6-Bis [3-(3-carboxymethylphenyl)-4-(2-α-D-mannopyranosyloxy)-phenyl] hexane (compound of formula (I)), FORM 6, is prepared according to a method generally known to the person skilled in the art by freeze drying a methanolic solution of FORM 1 at a concentration of 20 mg/ml or by dissolving FORM 3 in an acetone water mixture and freeze drying of the clear solution.

Example 13

Generation of FORM 6 of Compound of Formula (I)

The amorphous form of 1,6-Bis [3-(3-carboxymethylphenyl)-4-α-D-mannopyranosyloxy)-phenyl] hexane, FORM 6, is prepared according to the methods known to the person skilled in the art by lyophilisation of a mixture of FORM 1 and FORM 2. 100 mg of material was dissolved in a minimum amount of aceone/water (1:1; 40 ml) or t-butanol (50 ml) at 50° C. with shaking to ensure complete dissolution. The sample was then hot filtered and rapidly cooled to −78° C., before being lyophilised overnight to remove the solvent.

Example 14

Generation of FORM 6 of Compound of Formula (I)

The amorphous form of 1,6-Bis [3-(3-carboxymethylphenyl)-4-(2-α-D-mannopyranosyloxy)-phenyl] hexane (compound of formula (I)), FORM 6, is prepared according to the methods known to the person skilled in the art by fast evaporation of a mixture of FORM 1 and FORM 2. 100 mg of material was dissolved in 15 ml of methanol, before being filtered to remove any remaining crystals. The sample was then evaporated at 50° C. in vacuo in order to remove the solvent as quickly as possible.

Example 15

Preparation of a Microemulsion of FORM 1 of Compound of Formula (I)

1650 g of a microemulsion having the following composition was prepared according to the methods known to the person skilled in the art by mixing 1.0% of FORM 1 of 1,6-Bis [3-(3-carboxymethylphenyl)-4-(2-α-D-mannopyranosyloxy)-phenyl] hexane, 8% of Tagat® O2 V (surfactant, Goldschmidt GmbH), 12% of Synperonic® PE/L101 (Poloxamer 331, surfactant, Uniqema), 5% of glyceryl triacetate (Triacetin), and qs100% of propylene glycol/0.005 N hydrochloric acid (2:1). The pH value of the formula was adjusted to 4.0. Preparation of the microemulsion employing FORM 1, which shows highest solubility in both propylene glycol and Triacetin as compared to other FORMS, gave best results.

The claimed invention is:

1. 1,6-Bis [3-(3-carboxymethylphenyl)-4-(2-α-D-mannopyranosyloxy)-phenyl] hexane monohydrate having the chemical formula:

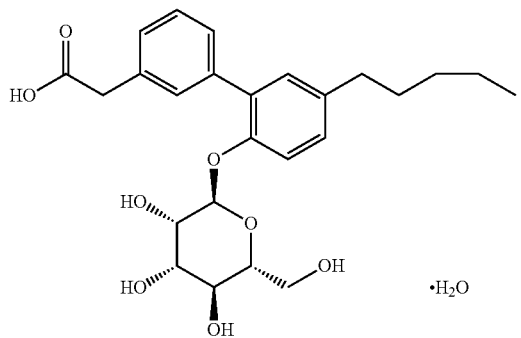

·H$_2$O

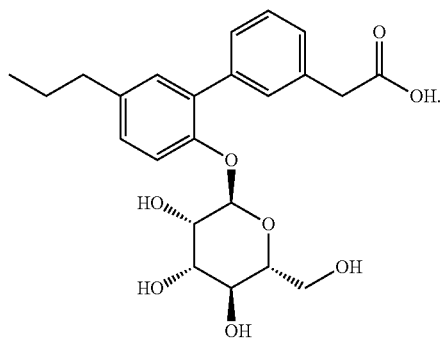

2. Crystalline 1,6-Bis [3-(3-carboxymethylphenyl)-4-(2-α-D-mannopyranosyloxy)-phenyl] hexane monohydrate having the chemical formula of claim 1.

Figure 2:
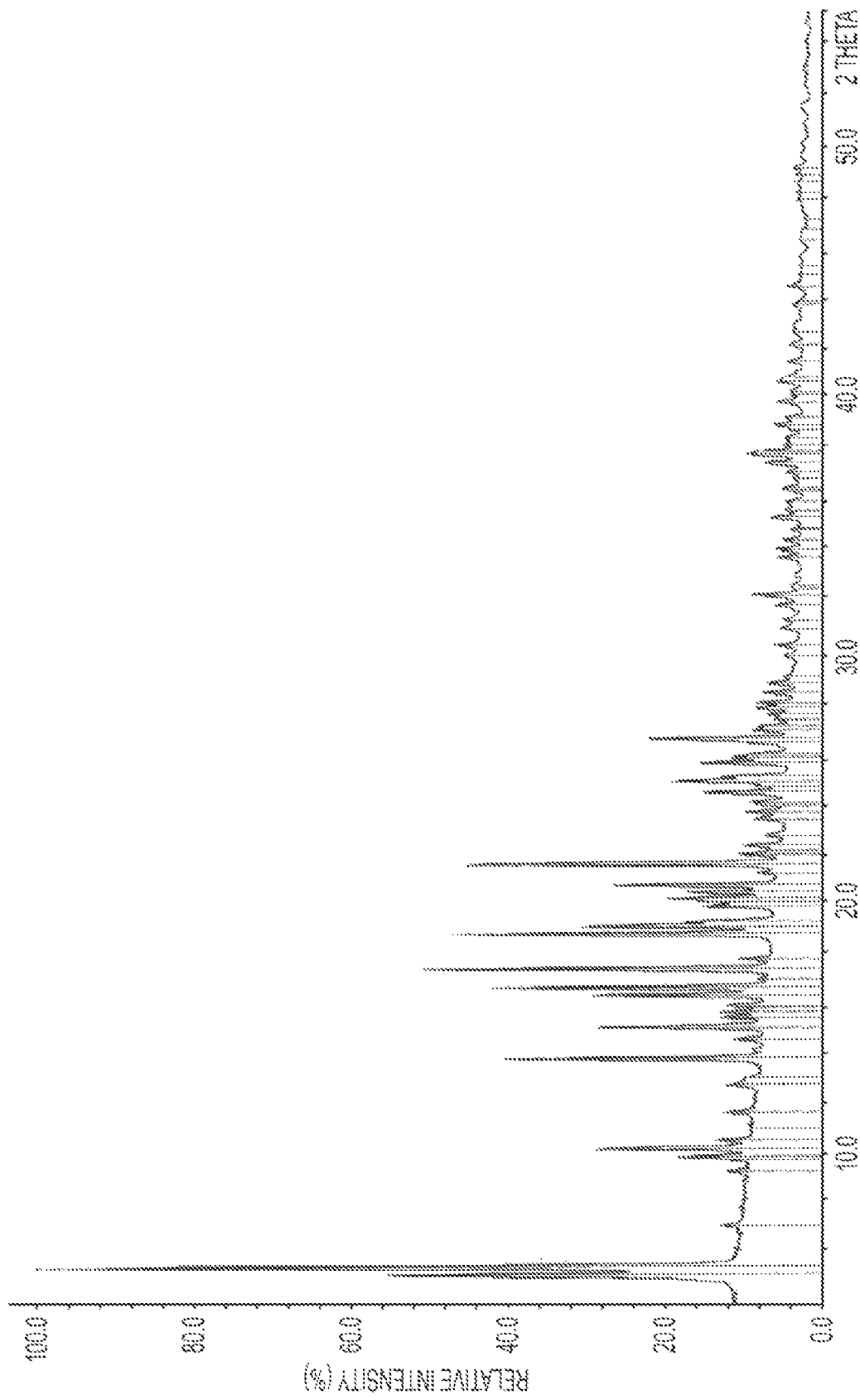
FIG. 2 shows the crystalline modification of Form 2 with the Relative Intensity (in %) shown as a function of 2Theta.
Figure 3:
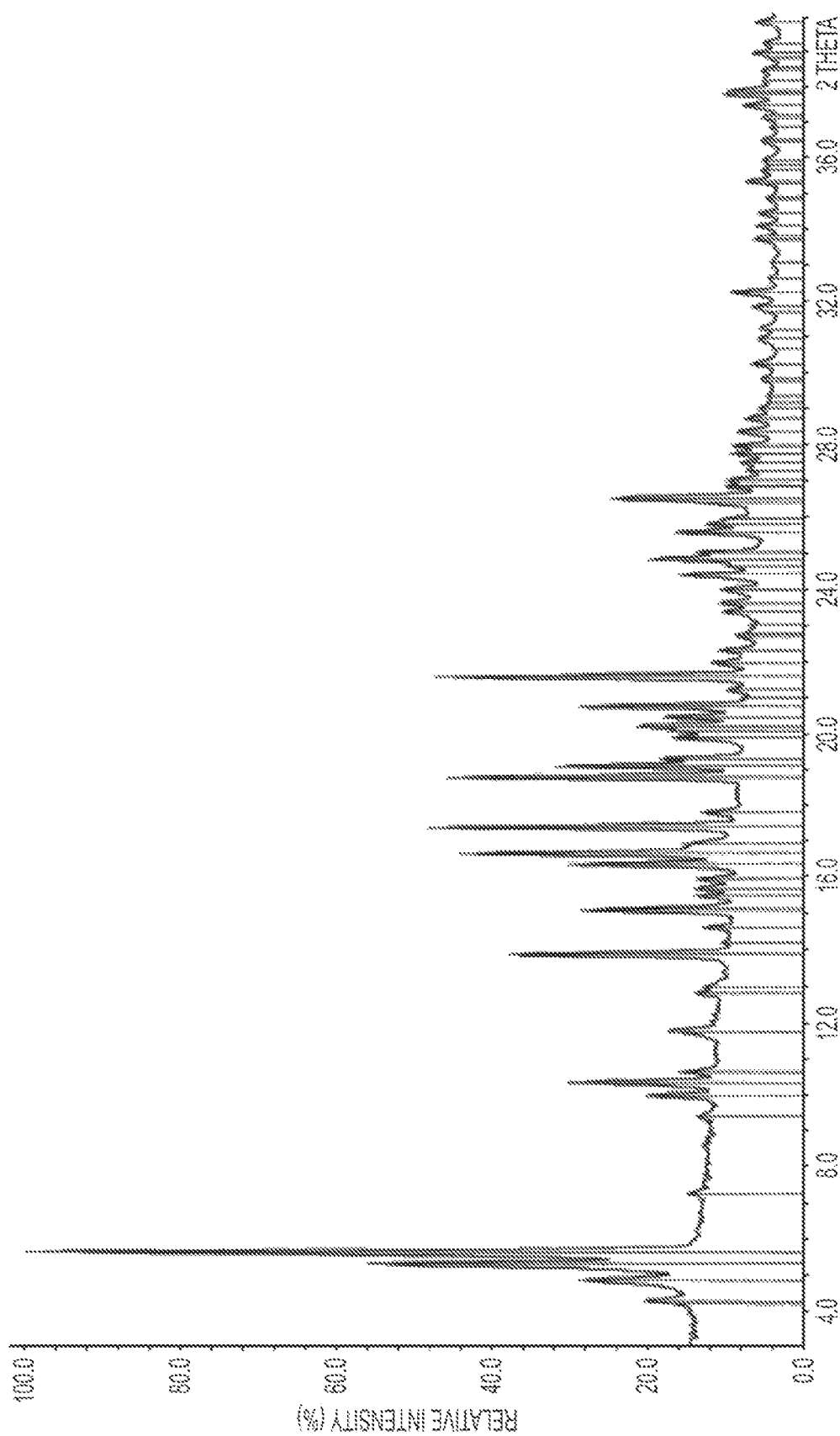
FIG. 3 shows the crystalline modification of Form 3 with the Relative Intensity (in %) shown as a function of 2Theta.
Figure 4:
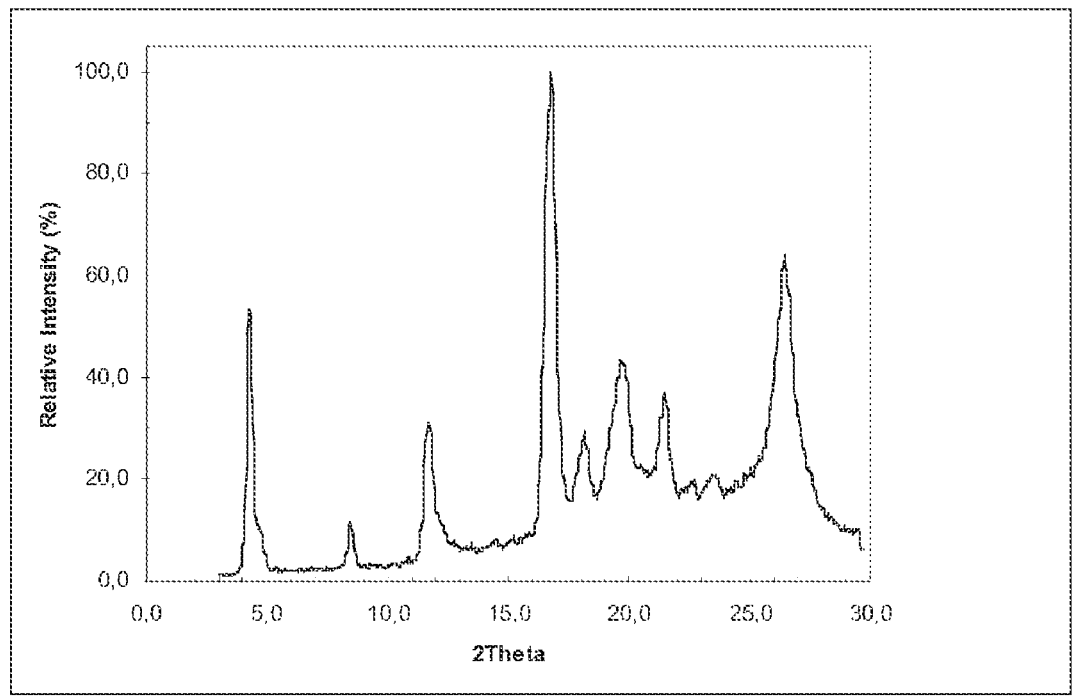
FIG. 4 shows the crystalline modification of Form 4 with the Relative Intensity (in %) shown as a function of 2Theta.
Figure 5:
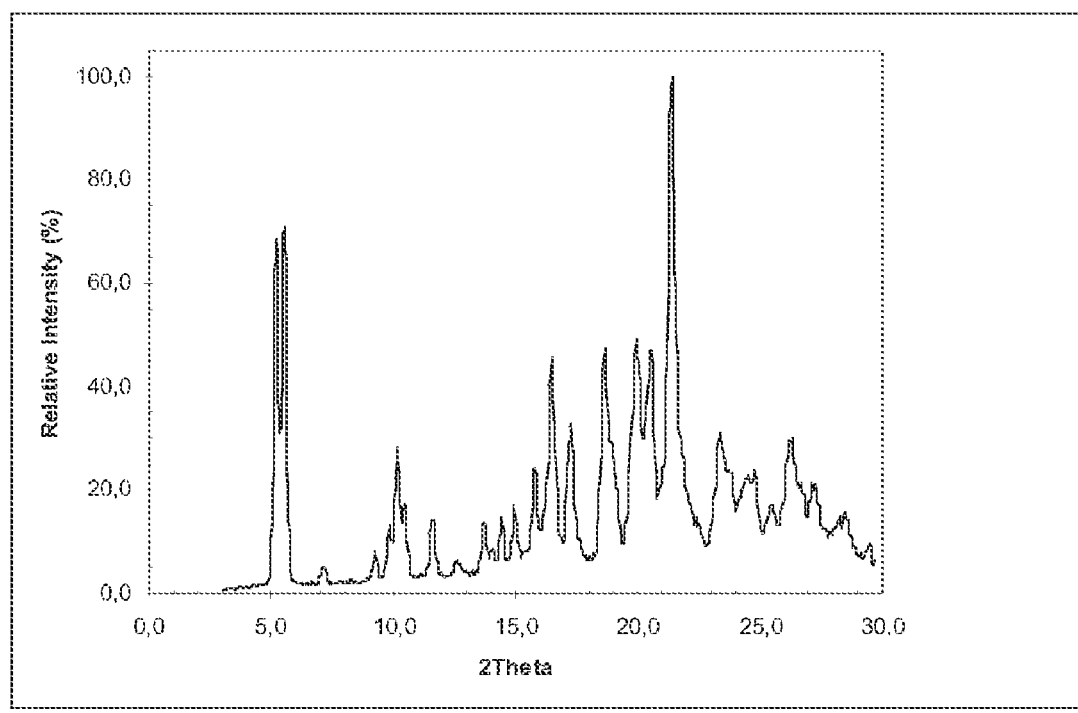
FIG. 5 shows the crystalline modification of Form 5 with the Relative Intensity (in %) shown as a function of 2Theta.
Figure 6:
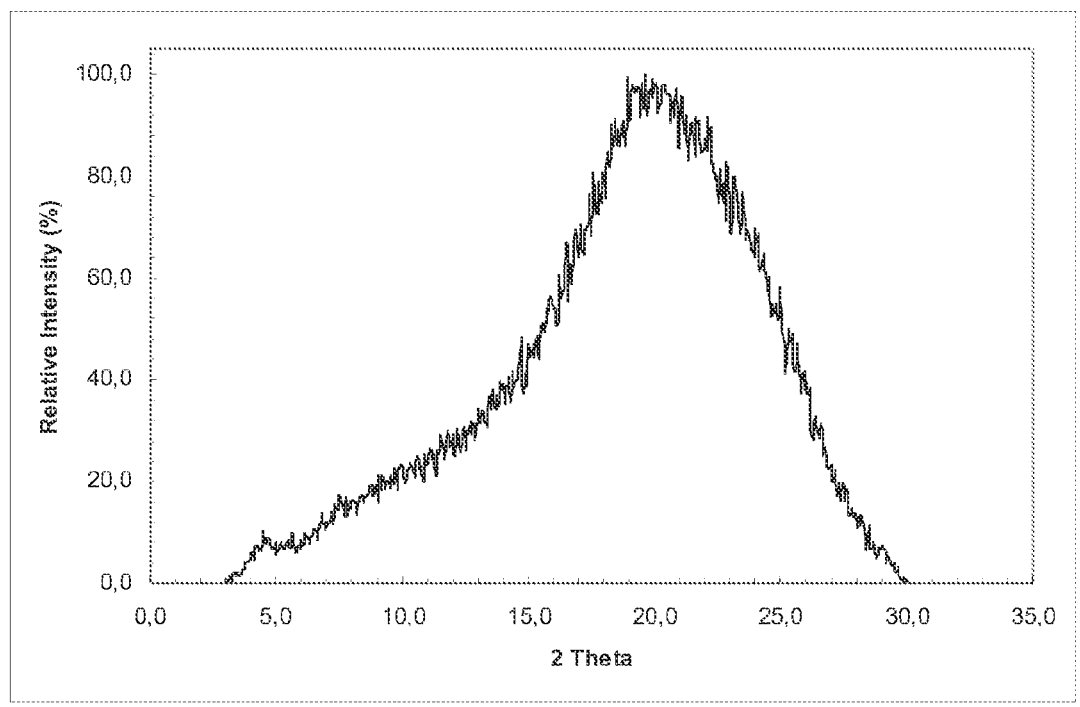
FIG. 6 shows the modification of Form 6 with the Relative Intensity (in %) shown as a function of 2Theta.
Figure 7:
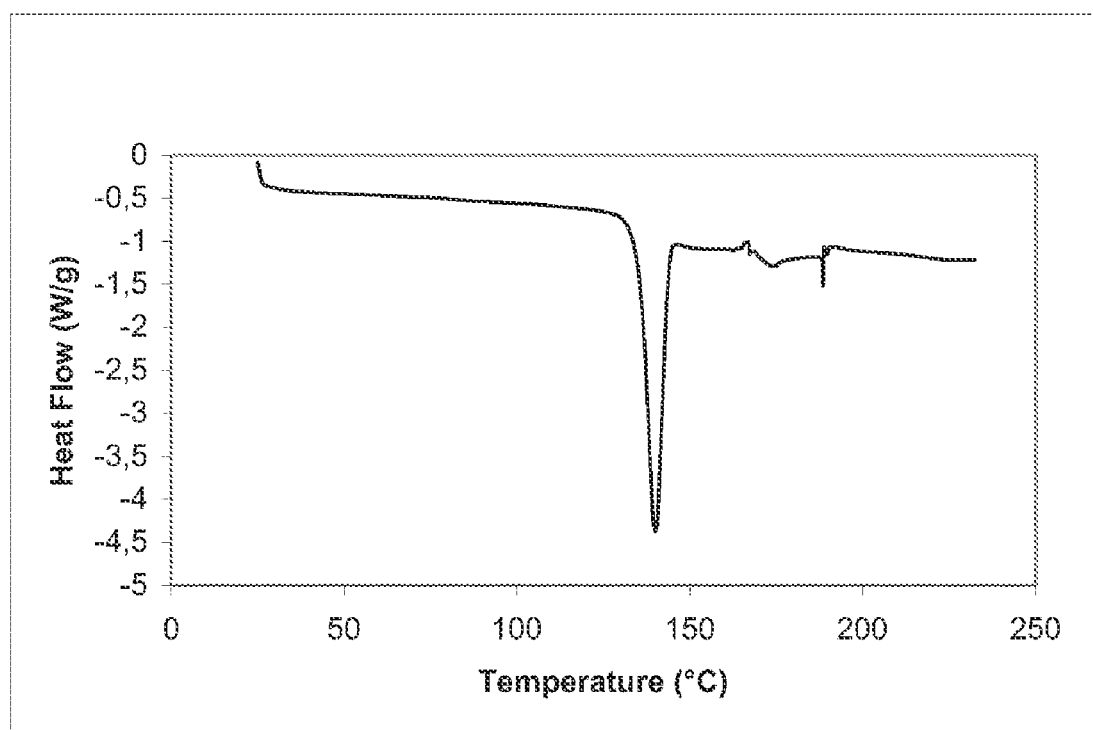
FIG. 7 shows the Differential Scanning Calorimetry (DSC) of Form 1. The Heat Flow (in W/g) is shown as a function of temperature (in °C.).
Figure 8:
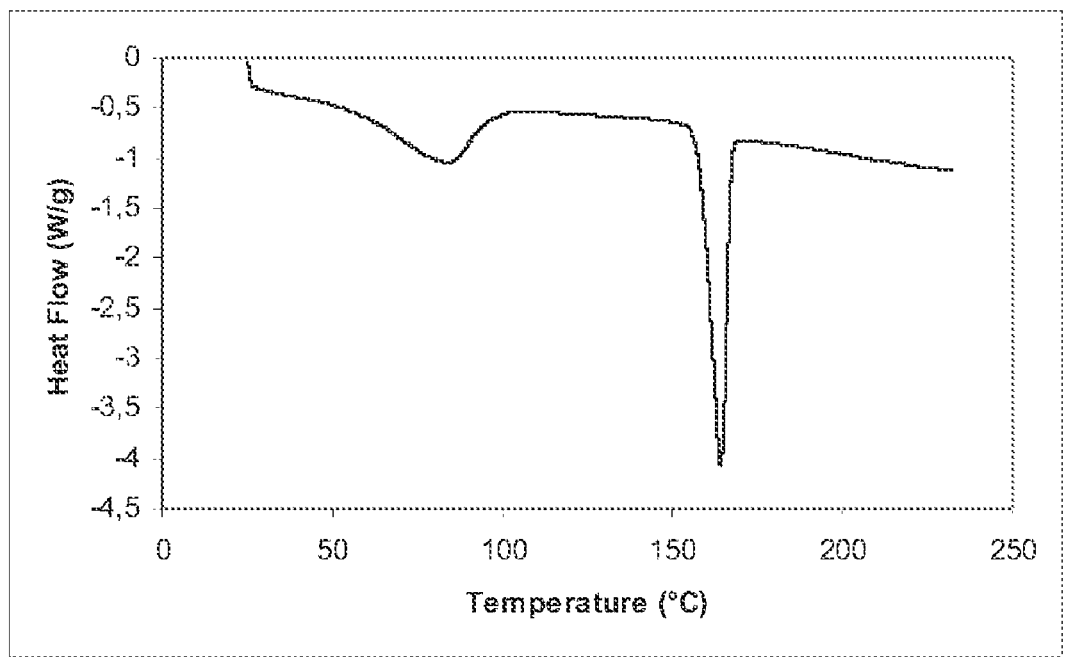
FIG. 8 shows the Differential Scanning Calorimetry (DSC) of Form 2
Figure 9:
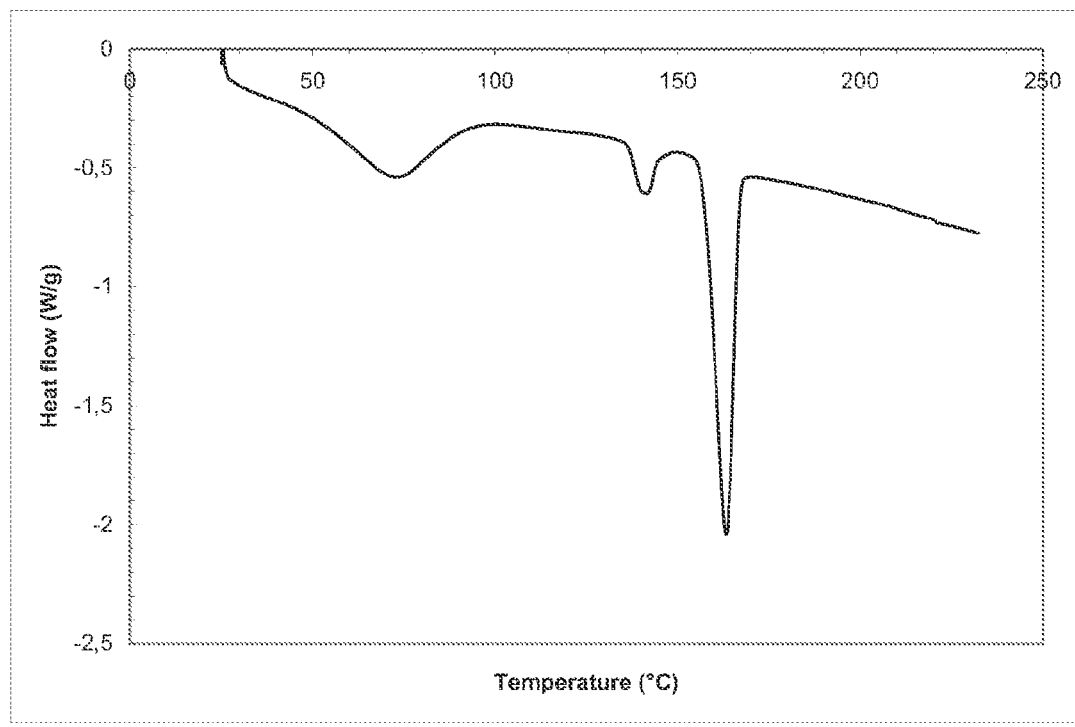
FIG. 9 shows the Differential Scanning Calorimetry (DSC) of Form 3
Figure 10:
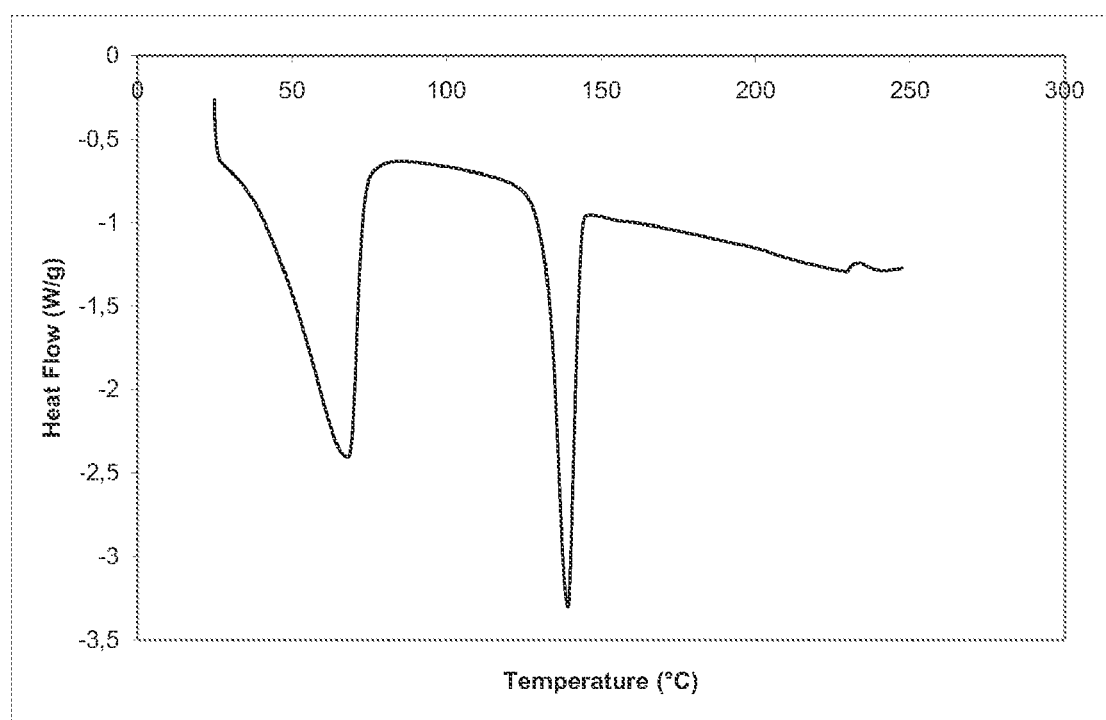
FIG. 10 shows the Differential Scanning Calorimetry (DSC) of Form 4
Figure 11:
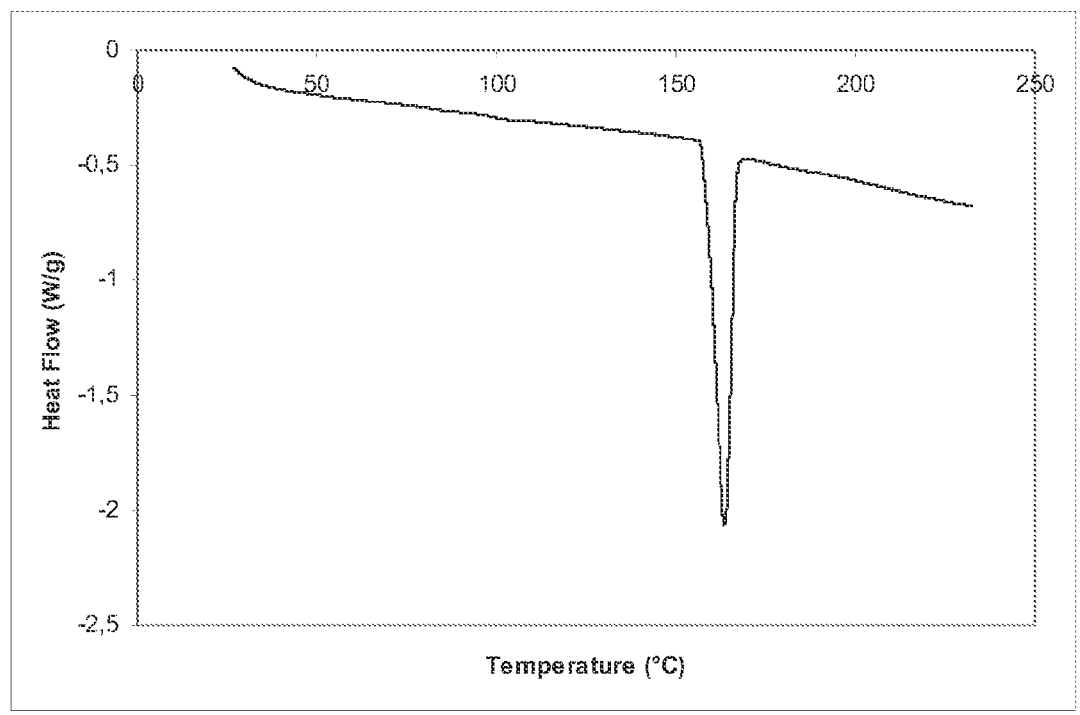
FIG. 11 shows the Differential Scanning Calorimetry (DSC) of Form 5
Figure 12:
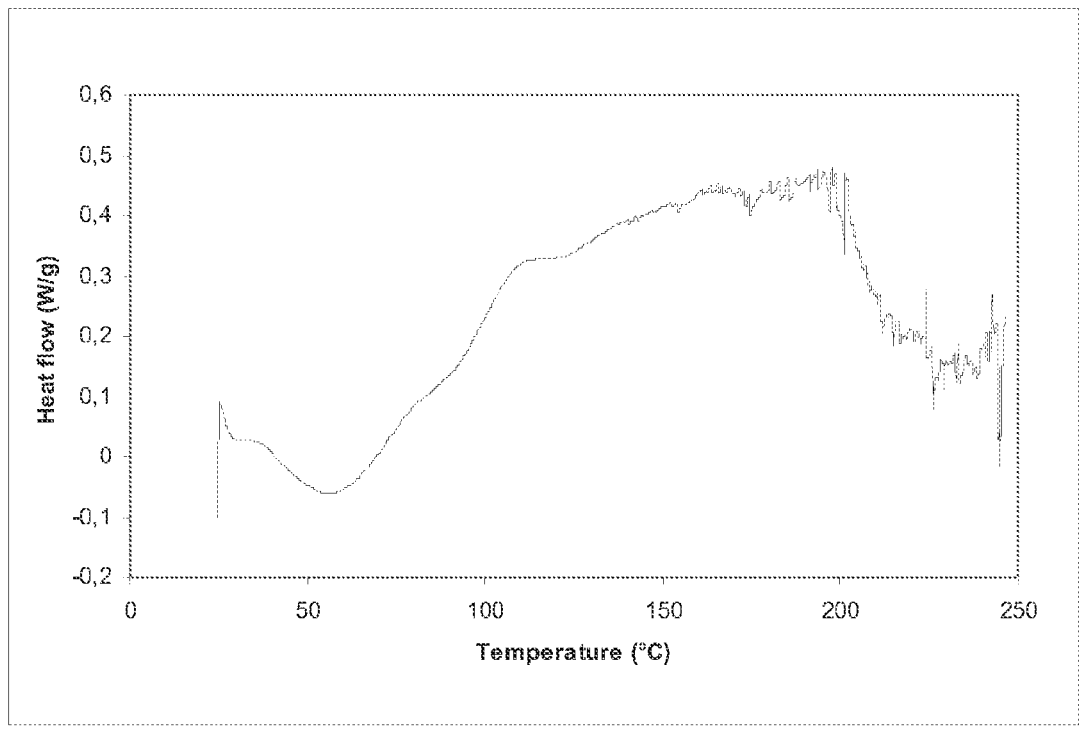
FIG. 12 shows the Differential Scanning Calorimetry (DSC) of Form 6
Figure 13:
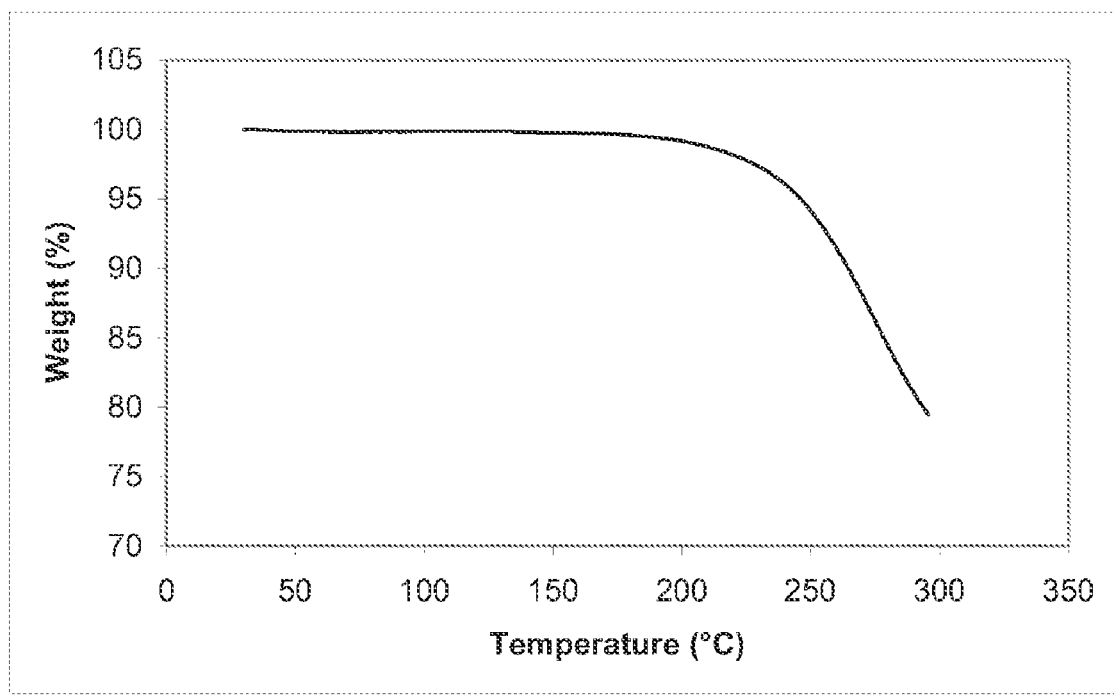
FIG. 13 shows the results of a Thermo-Gravimetric Analysis (TGA) of Form 1 The weight (in %) is shown as a function of temperature (in °C.).
Figure 14:
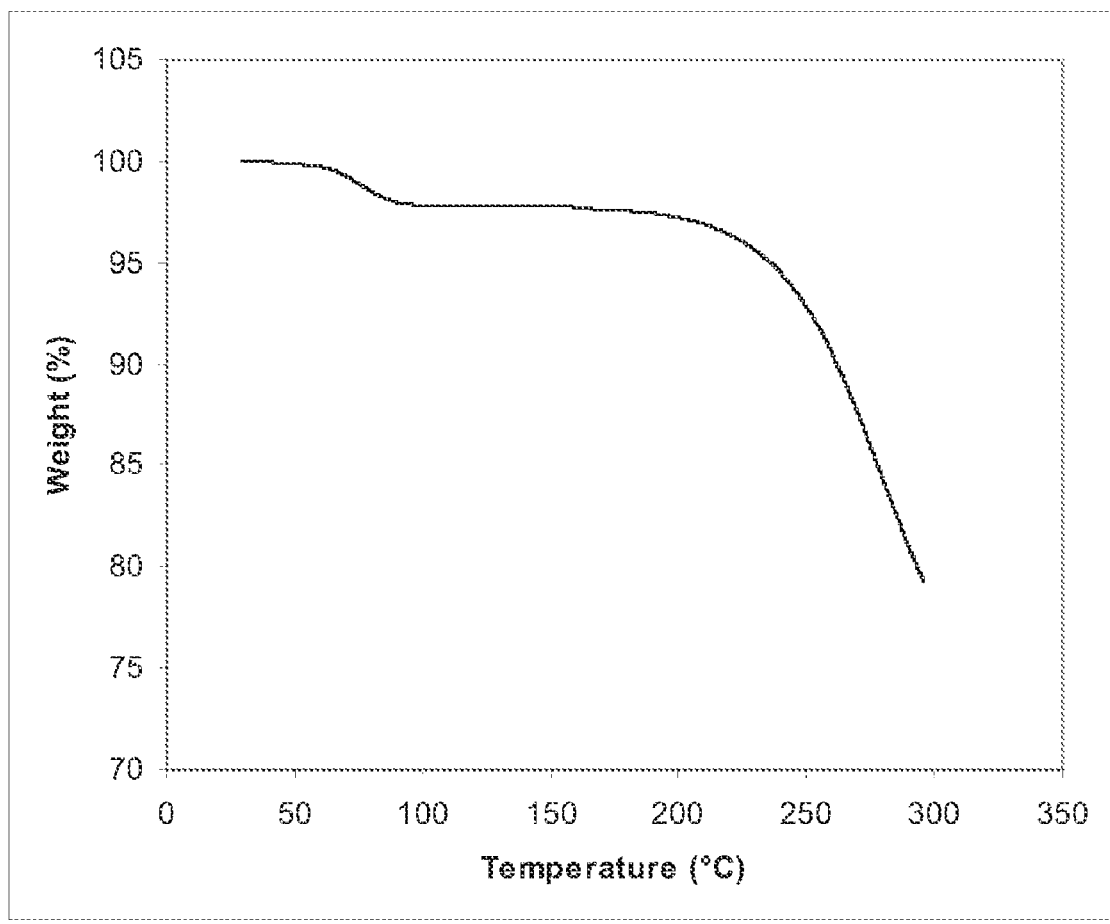
FIG. 14 shows the results of a Thermo-Gravimetric Analysis (TGA) of Form 2
Figure 15:
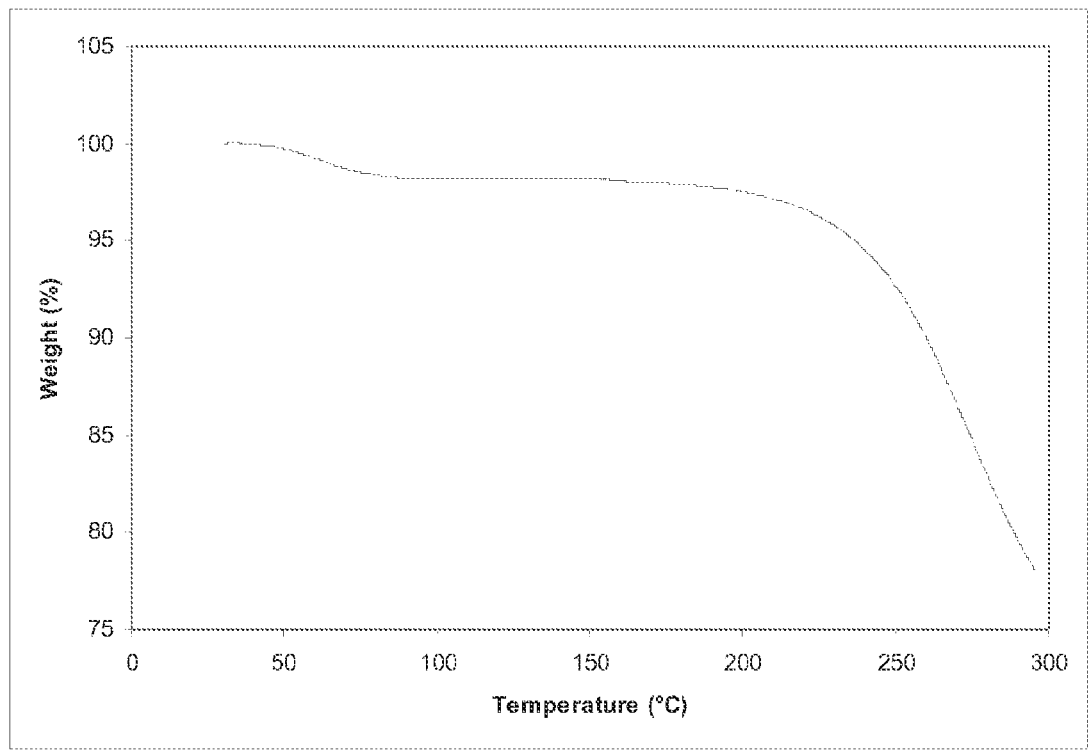
FIG. 15 shows the results of a Thermo-Gravimetric Analysis (TGA) of Form 3
Figure 16:
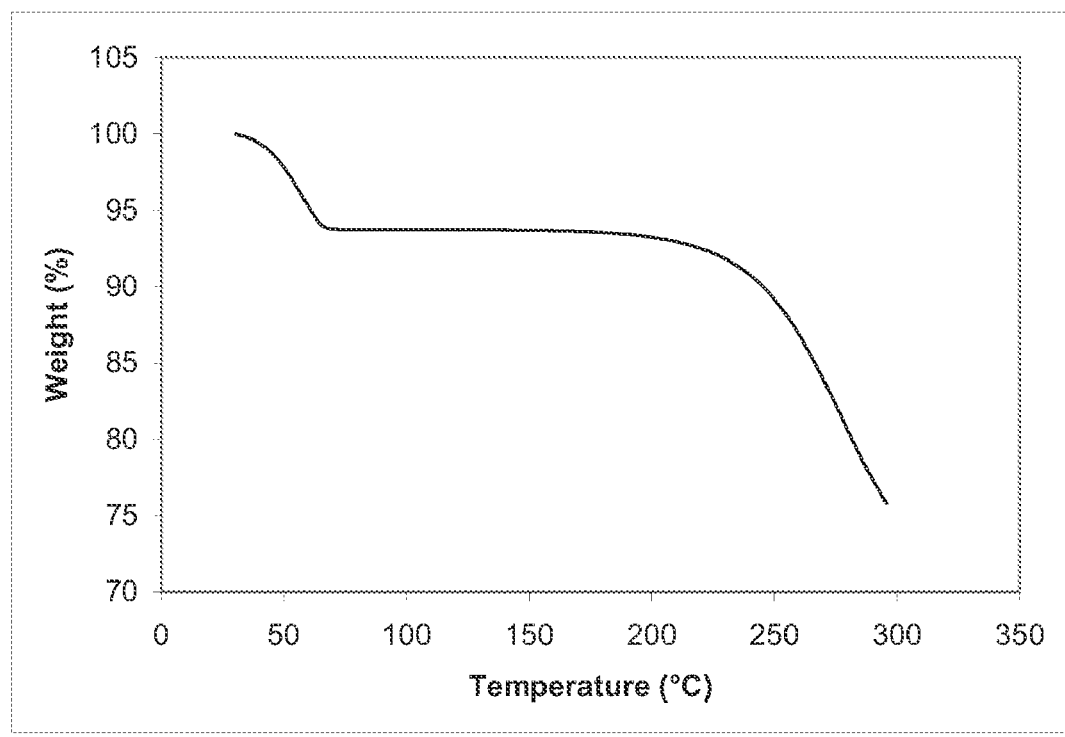
FIG. 16 shows the results of a Thermo-Gravimetric Analysis (TGA) of Form 4

3. Crystalline 1,6-Bis [3-(3-carboxymethylphenyl)-4-(2-α-D-mannopyranosyloxy)-phenyl] hexane monohydrate of claim 2, characterized by at least one of:

an X-ray powder diffraction pattern having diffraction angles (2Theta) based on cupric K$_{α1}$ at approximately 5.3° 2Theta, 5.6° 2Theta, 17.4° 2Theta, and 15.1° 2Theta;

an X-ray powder diffraction pattern as substantially shown in FIG. 2; and an infrared spectrum containing peaks at 3246 cm$^{-1}$, 2933 cm$^{-1}$, 1728 cm$^{-1}$, 1478 cm$^{-1}$, 1226 cm$^{-1}$, 1066 cm$^{-1}$; 1017 cm$^{-1}$, 982 cm$^{-1}$, 800 cm$^{-1}$; 686 cm$^{-1}$, and 605 cm$^{-1}$.

4. A pharmaceutical composition comprising 1,6-Bis [3-(3-carboxymethylphenyl)-4-(2-α-D-mannopyranosyloxy)-phenyl] hexane monohydrate of claim 1 and at least one further pharmaceutically acceptable component.

5. A pharmaceutical composition comprising crystalline 1,6-Bis [3-(3-carboxymethylphenyl)-4-(2-α-D-mannopyranosyloxy)-phenyl] hexane monohydrate of claim 2 and at least one further pharmaceutically acceptable component.

6. A pharmaceutical composition comprising crystalline 1,6-Bis [3-(3-carboxymethylphenyl)-4-(2-α-D-mannopyranosyloxy)-phenyl] hexane monohydrate of claim 3 and at least one further pharmaceutically acceptable component.

* * * * *